US006312727B1

(12) United States Patent
Schacht et al.

(10) Patent No.: US 6,312,727 B1
(45) Date of Patent: Nov. 6, 2001

(54) DELIVERY OF NUCLEIC ACID MATERIALS

(76) Inventors: Etienne H Schacht, Rijsseveldstraat 99, B-8140, Staden (BE); Leonard C W Seymour, The University of Birmingham, Clinical Research Block, The Medical School, Edgbaston, Birmingham B15 2TJ (GB); Karel Ulbrich, Inst of Macromolecular Chemistry, Academy of Sciences of the Czech Republic, Heyrovsky Sq. 2, 16206, Prague 7 (CZ)

(*) Notice: Subject to any disclaimer, the term of this patent is extended or adjusted under 35 U.S.C. 154(b) by 0 days.

(21) Appl. No.: 09/306,568

(22) Filed: May 6, 1999

Related U.S. Application Data

(63) Continuation of application No. PCT/GB97/02965, filed on Nov. 6, 1997.

(30) Foreign Application Priority Data

Nov. 6, 1996 (GB) .................................................. 9623051

(51) Int. Cl.[7] .............................. A61K 9/51; C12N 15/63; C12N 15/85; C07H 21/04
(52) U.S. Cl. ...................... 424/490; 424/493; 435/320.1; 435/455; 536/23.1
(58) Field of Search ................................... 424/490, 493; 435/320.1, 455; 514/44; 536/23.1

(56) References Cited

U.S. PATENT DOCUMENTS 5,661,025 * 8/1997 Szoka et al. .......................... 435/458
5,714,166 * 2/1998 Tomalia et al. ....................... 424/486
5,837,533 * 11/1998 Boutin et al. ..................... 435/320.1

OTHER PUBLICATIONS

Wolfert et al. Characterization of vectors for gene therapy formed by self–assembly of DNA with synthetic block co–polymers. Human Gene Therapy. vol. 7:2123–2133, Nov. 1996.*

Orkin et al. Report and recommendations of the panel to assess the NIH investment in research on gene therapy, Dec. 1995.*

Anderson, WF Human gene therapy. Nature vol. 392 (supp) 25–30, Apr. 1998.*

Verma et al. Gene therapy—promises, problems and prospects. Nature vol. 389:239–242, Sep. 1997.*

Marshall, E. Gene therapy's growing pains. Science vol. 269:1050–1055, Aug. 1995.*

* cited by examiner

*Primary Examiner*—Terry McKelvey
*Assistant Examiner*—William Sandals
(74) *Attorney, Agent, or Firm*—Pillsbury Winthrop LLP

(57) ABSTRACT

Synthetic polymer-based carrier vehicles for delivery of nucleic acid material to target cells in biological systems are made by self-assembly of the nucleic acid with cationic polymer material so as to condense the nucleic acid and form a polyelectrolyte complex and reacting the complex with hydrophilic polymer material which bonds to the complex forming a hydrophilic coating that stabilizes the complex and provides an outer protective steric shield. The carrier vehicles are useful for gene therapy.

52 Claims, 11 Drawing Sheets

A. Vector components

1. DNA expression vector

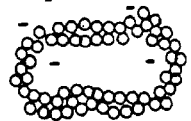

2. Bioactive component e.g. membrane penetration

3. Modified cationic polymers

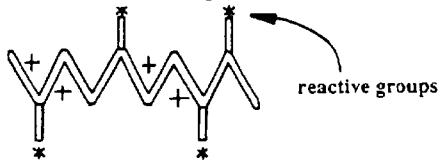
reactive groups

4. Reactive hydrophilic polymer for coating and stabilisation

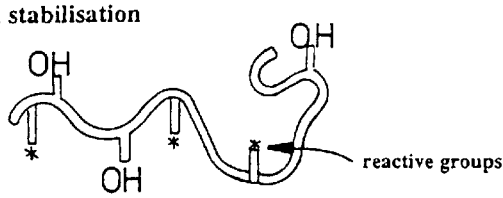
reactive groups

5. Monofunctional biotinylated hydrophilic polymer

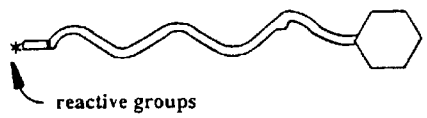
reactive groups

B. Vector assembly

1+2+3 ⟶ 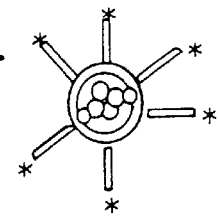

+4+5

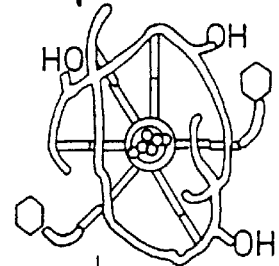

+ streptavidin-antibody

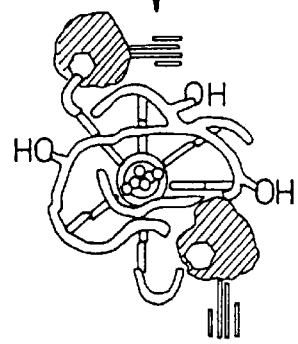

C. Important stages in the targeted delivery of DNA (1) Stability and prolonged circulation in ther blood.
(2) Extravasation in target tissue
(3) Target recognition.
(4) Internalisation.
(5) Escape from the endosome

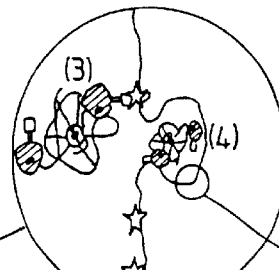
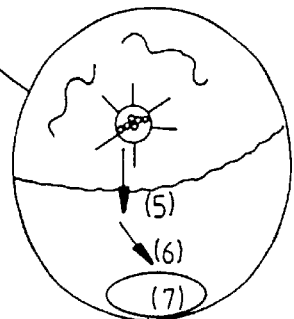

(6) Translocation and entry into the nucleus.
(7) Efficient transcription.

Schematic diagram of the chemical reactions in Example 7

1st Stage

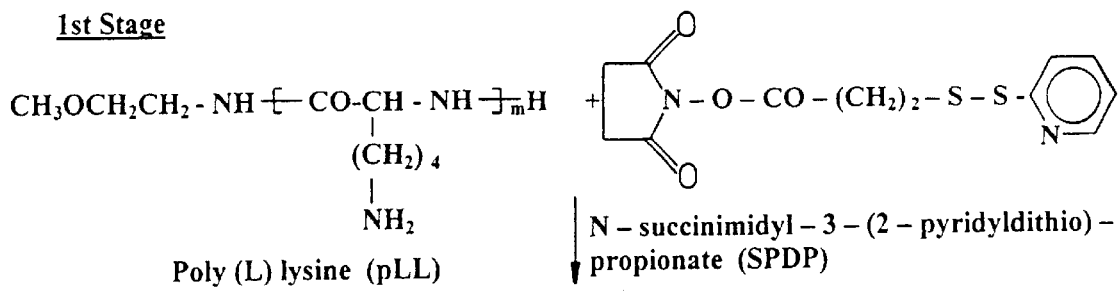

Poly (L) lysine (pLL)

N – succinimidyl – 3 – (2 – pyridyldithio) – propionate (SPDP)

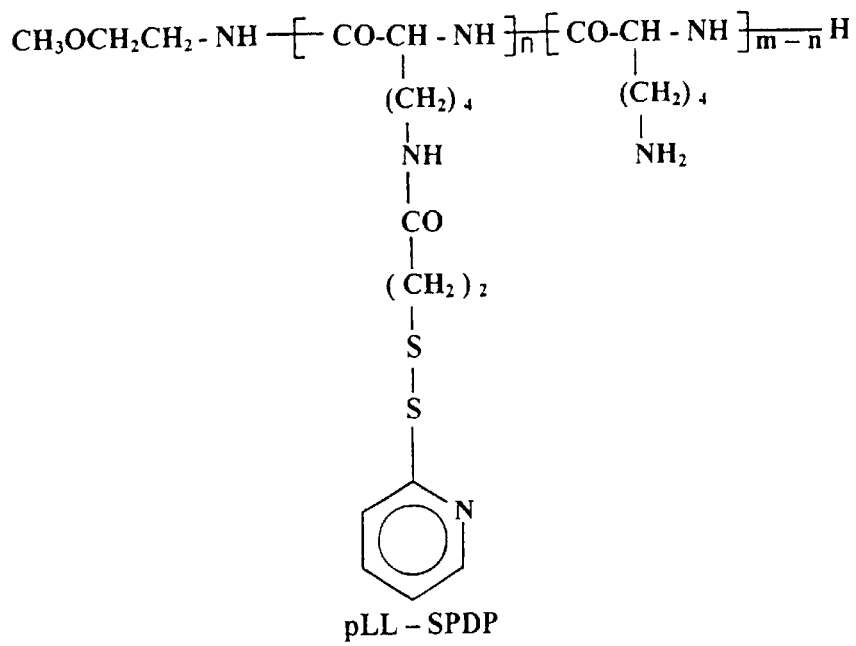

pLL – SPDP

2nd Stage

partially modified pLL – SPDP + DNA ⟶ polyelectrolyte complex (partially modified pLL/DNA)

3rd Stage

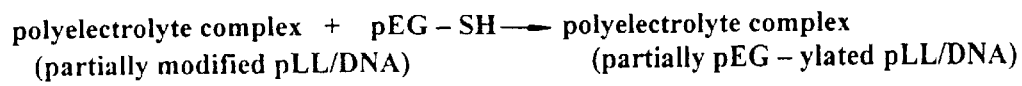

polyelectrolyte complex + pEG – SH ⟶ polyelectrolyte complex
(partially modified pLL/DNA)            (partially pEG – ylated pLL/DNA)

Structure of the alternating poly(ethyleneglycol)-oligopeptide block copolymer n = 45 approx., x = 8 approx., pEG blocks Mw 2000 approx.

1. Synthesis of pHEG-ONp pHEG
with R=4-nitrophenyl; 4-nitrobenzyl; benzyl; phenyl; 2,2,2-trichlor 2. Synthesis of pHEG-succinate and subsequent conversion to its N-hydroxysuccinimide ester pHEG

FIG. 7B
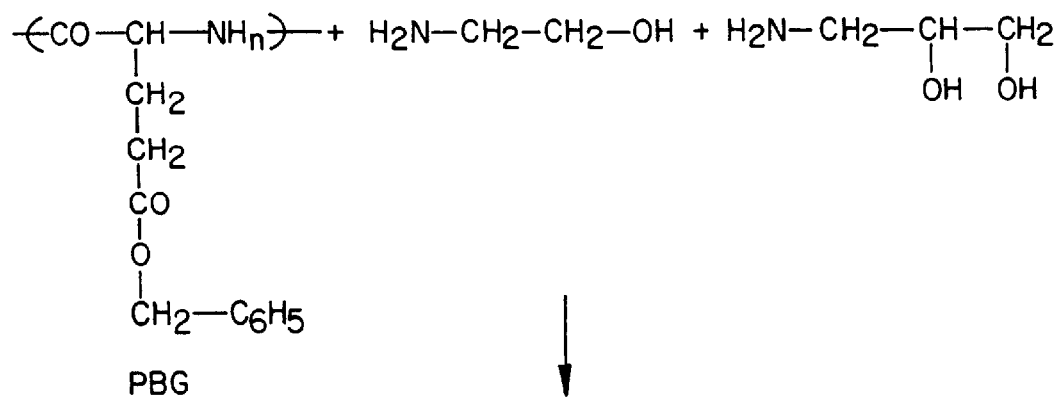
PBG
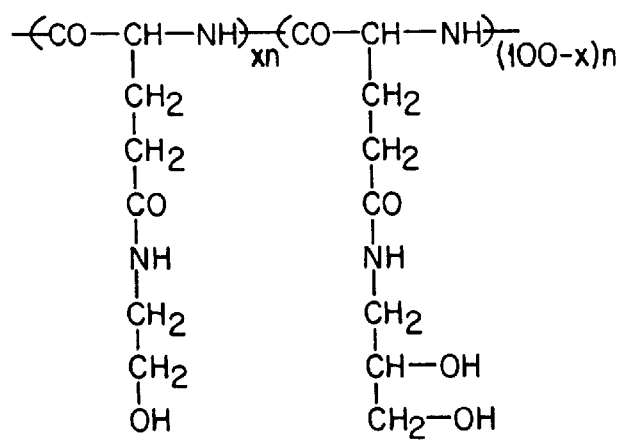
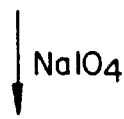
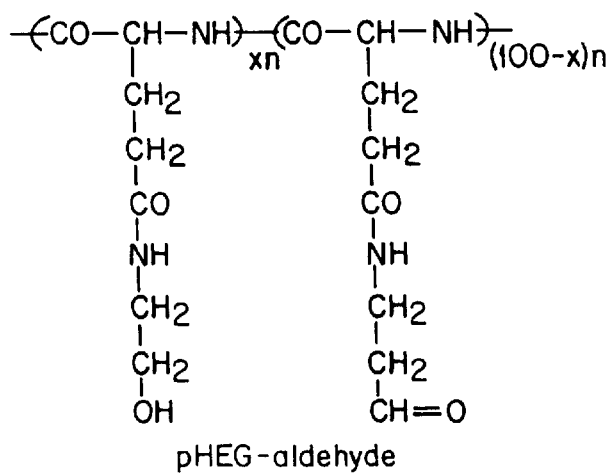
pHEG-aldehyde

FIG. 9
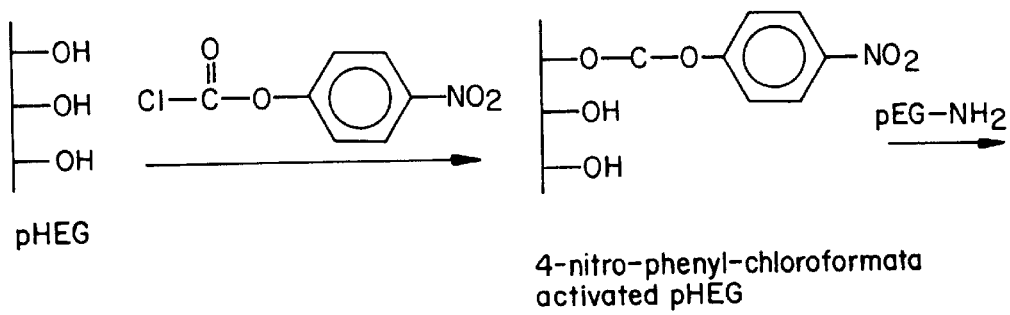
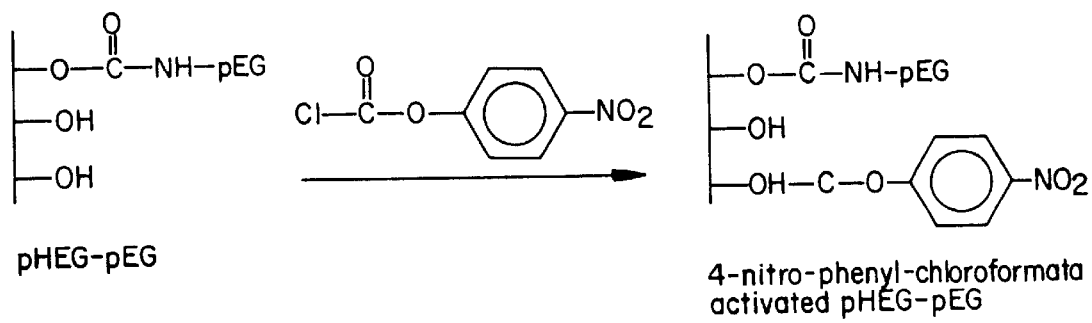
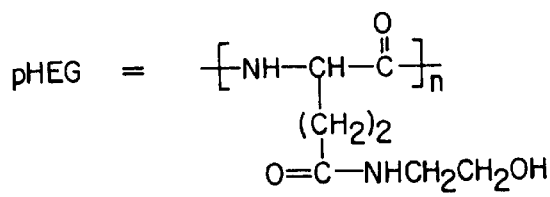
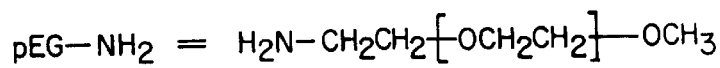

FIG. 10
pLL-g-pEG via -s- bond
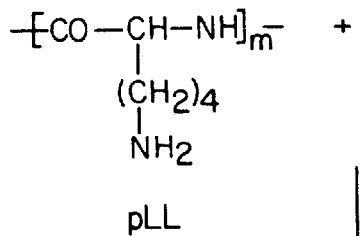
pLL
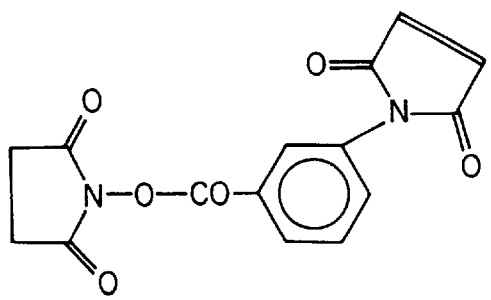
MBS
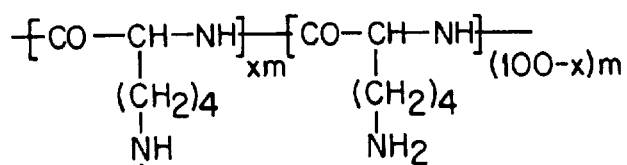
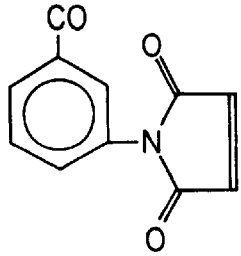
↓ fusogenic peptide -SH
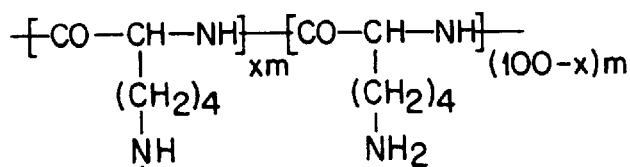
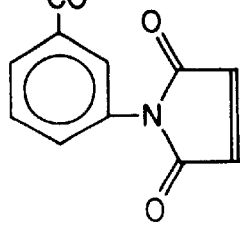
—S— fusogenic peptide pLL-g-pEG via labile -S-S-bond

DELIVERY OF NUCLEIC ACID MATERIALS

This application claims priority to application No. 9623051.1 filed Nov. 6, 1996 in the United Kingdom. This is a Continuation of: International Application No. PCT/GB97/02965 filed Nov. 6, 1997.

The present invention relates to the delivery of nucleic acid material to target cells in biological systems and to the construction of delivery vehicles for this purpose, especially in connection with gene therapy.

BACKGROUND

The possibility of delivering genes into somatic cells raises many promising new therapeutic opportunities, although the difficulty of efficient delivery to target cells in vivo currently represents a major barrier to progress. Despite the range of techniques available for in vitro transfection of cells, many of these techniques e.g. calcium phosphate precipitation, electro-permeabilisation, etc., cannot be applied in vivo; most animal and clinical studies have relied on the use of liposomal or viral vectors. Cationic liposomes have shown some success in vivo, particularly via non-systemic routes, but they are poorly defined and their net charge is thought to inhibit effective systemic delivery because it promotes binding to plasma proteins and to extracellular matrix. At present viruses provide the most popular vectors for in vivo delivery, particularly with improved DNA packaging techniques. However, their inherent immunogenicity, possibility of fixing complement, poor target-selectivity and difficulty of scale-up production, together with concerns over potential toxicity, seem likely to prevent their widespread acceptance and licensing. There is therefore a clear need for alternative safe and efficient DNA or gene delivery systems, preferably based on fully synthetic carrier vehicles.

A synthetic carrier vehicle or vector suitable for efficient targeted delivery of DNA or other nucleic acid material in vivo must fulfil various biological requirements. Ideally it would be stable in the blood circulation, non-immunogenic and resistant to enzymatic degradation, capable of efficient target-discrimination, and able to penetrate the target cell membrane selectively to gain access to the nucleus, release the nucleic acid and enable efficient transcription within the target cell.

One approach to the development of synthetic vectors or carrier vehicles for delivery of DNA has been proposed based on soluble cationic polymers designed to self-assemble with DNA of expression vectors, it having been shown previously that DNA can be condensed into polyelectrolyte complexes by the addition of polycations, rendering it easier to package. For example, simple mixing of DNA with poly(L)lysine results in formation of discrete polyelectrolyte particles whose size and capacity for spontaneous transfection can be influenced by the molecular weight of the poly(L)lysine used. Specific cell targeting groups, e.g. transferrin and/or membrane-permeabilising groups such as membrane disrupting oligopeptides, can be incorporated into such structures and significantly enhance the transfection rates achieved.

These simple polyelectrolyte DNA complexes are of limited usefulness, however, for systemic administration due to rapid clearance following intravenous (i.v.) injection although the exact reasons for this rapid clearance are not fully understood. However, it does appear that these simple DNA/cationic polymer complexes are subject to destabilisation by serum proteins, especially albumin at physiological concentrations, and may be subject to degradation by serum nucleases, despite their relative stability compared with free DNA.

For successful and versatile in vivo application it is very important that nucleic acid delivery vehicles should be small enough to gain access to target cells. Access to target cells frequently involves extravasation through endothelial layers, but even the hyper-permeable endothelia associated with tumours have a size restriction of about 70 nm. In addition, most forms of triggered membrane penetration act via the endosomal membrane following endocytosis, and endocytic internalisation is usually limited to materials of less than 100 nm diameter. Given the large size of DNA expression vectors in free solution (typical diameter 200 nm) it is clearly necessary for the DNA to be compressed and packaged during self-assembly with cationic polymers if the polyelectrolyte complexes thereby formed are to provide satisfactory DNA carriers and delivery vehicles.

One object of the present invention is to provide improved synthetic polymer-based polyelectrolyte vectors to serve as carrier vehicles for efficient and effective delivery of nucleic acid material, and transfection of target cells, especially in connection with gene therapy or even possibly in connection with development of DNA vaccines.

SUMMARY OF THE INVENTION

Preparation of synthetic polyelectrolyte vectors or nucleic acid carrier vehicles in-accordance with the invention will usually involve forming a complex having a nucleic acid-containing core portion by self-assembly between cationic polymer material and nucleic acid material, especially DNA contained in an expression vector, said core portion being provided, directly or indirectly, with various other functional molecules or molecular entities including molecules of hydrophilic polymer material that provide a coating and steric shield for the core portion, thereby improving stability and biocompatibility of the polyelectrolyte complex. In one technique, this may be achieved by synthesising or modifying a soluble synthetic cationic polymer so as to include or incorporate therein discrete reactive groups prior to arranging a selective self-assembly of such polymer with the nucleic acid material. This self-assembly with the nucleic acid involves an association or binding between molecules of the polycationic component and the polyanionic nucleic acid component. In the complex so formed, the nucleic acid is condensed in the core portion and at least some of said reactive groups on the molecules of the cationic polymer component are presented at the surface thereof. These reactive groups can then be coupled or linked with hydrophilic polymer molecules that associate with the solvent and form in effect an outer shield around the polymer nucleic acid complex, thereby improving stability of the complex and presenting a hydrophilic steric barrier to interactions with cells and molecules which may be encountered in the course of in vivo gene therapy, e.g. while circulating in the plasma after i.v. administration.

In some preferred embodiments the hydrophilic polymer molecules will be multivalent, i.e. will include multiple reactive groups, so that after a first reactive group binds to a reactive group of the cationic polymer and "anchors" the hydrophilic polymer other reactive groups of the latter will bind to other reactive groups of the cationic polymer, thereby cross-linking the coating or outer surface at the same time as providing a steric shielding of the nucleic acid polycation complex.

It will be understood that the term "reactive group" is used herein to denote a group that shows significant chemical reactivity, especially in relation to coupling or linking reactions with complementary reactive groups of other molecules. Also, the terms cationic and anionic denote materials which in aqueous solution at neutral pH have net positive and negative charges respectively.

Thus, as will hereinafter become apparent, the invention provides a nucleic acid carrier vehicle for delivery of nucleic acid material to target cells in biological systems, e.g. in vivo delivery of genes or therapeutic DNA to a patient in carrying out gene therapy or DNA vaccination treatment, said carrier vehicle being in the form of a polyelectrolyte complex comprising a nucleic acid-containing cationic polymer core associated with hydrophilic polymer material that forms an outer stabilising steric shield or coating. The cationic polymer core, which is generally made up of a plurality of polycation molecules, will usually also be linked, directly or indirectly, to other molecular entities or moieties, especially bioactive molecules, that modify the biological and/or physico-chemical characteristics of the complex to improve suitability for use in delivering the nucleic acid material to target cells, for example in carrying out somatic gene therapy treatment. These other molecular entities or moieties may comprise cell-receptor targeting moieties and/or other specific bioactive agents providing, for example, membrane disrupting agents, agents capable of promoting endocytic internalisation following binding to cell surface molecules, and nuclear-homing agents, useful for facilitating entry and delivery of the nucleic acid material, e.g. DNA, into cells. In particular, these other molecular species may include bioactive agents such as peptides, especially for example fiusogenic amphipathic helical peptides. One particular example of the latter is peptide material known under the designation INF7 supplied by Severn Biochemicals Limited.

Targeting groups as referred to above may include growth factors, antibodies or bibactive materials such as transferrin for example.

Nucleic acid carrier vehicles as referred to above in accordance with the invention may be constructed by means of a stepwise process in which the cationic polymer is first self-assembled with the nucleic acid material to form a complex that provides a core portion of the complete carrier vehicle, and the hydrophilic polymer material is then assembled in a subsequent step.

Thus, from one main aspect, the invention broadly provides a method of constructing a synthetic polymer-based carrier vehicle for delivery of nucleic acid material to target cells in biological systems, said method comprising the sequential steps of:

(a) bringing the nucleic acid material into association with cationic polyelectrolyte polymer material to form by self-assembly therebetween a polyelectrolyte complex which provides a nucleic acid containing cationic polymer core for said carrier vehicle, (b) reacting said polyelectrolyte complex with reactive hydrophilic polymer material so that the latter bonds to said complex and forms a hydrophilic coating that provides an outer protective steric shield and assists in stabilising the complex.

Although in some embodiments the hydrophilic polymer material of the coating associated with the nucleic acid-containing core of the complex may be bonded, at least partially, direct to the nucleic acid, for example via reactive carboxyl groups on the polymer binding to reactive hydroxyls of alcohol groups of the nucleic acid to form ester linkages that may subsequently be broken-down by acid-catalysed or hydrophilic degradation, in most embodiments it is presently preferred that the hydrophilic polymer material should be attached or linked directly only to the cationic polyelectrolyte polymer material of the nucleic acid-containing core by reactive groups which react with reactive groups of the cationic polymer material, usually, but not necessarily, to form covalent bonds. The reactive group or groups on the cationic polymer molecules for reacting with mutually reactive groups of the hydrophilic polymer will therefore usually be selected so as to have a reactivity not present in the nucleic acid material. Also, the reactive groups carried by the cationic polymer and/or by the hydrophilic polymer may often be carried by side chains of the polymer molecules and these side chains may be pH-sensitive and acid labile, hydrolytically unstable or enzymatically biodegradable as hereinafter described.

When the nucleic acid material and the cationic polyelectrolyte polymer material self-assemble to produce the polyelectrolyte complex reactive groups of the cationic polymer molecules will generally be exposed on the surface of the cationic polymer core, probably oriented outwardly, ready for reacting with the reactive hydrophilic polymer material in the subsequent stage. The outer protective steric shield provided by the hydrophilic coating not only assists in stabilising the complex but it can also protect the complex from unwanted biological interactions, e.g. in the course of in vivo gene therapy hen circulating in the plasma following administration by intravenous injection.

The other molecular entities mentioned that may be carried by the cationic polymer core, e.g. cell-receptor targeting moieties and/or other specific bioactive agents, may be coupled or linked directly to cationic polymer molecules of the nucleic acid-containing polyelectrolyte complexes, either the same cationic polymer molecules as are linked to the hydrophilic polymer material or different cationic polymer molecules, again via the aforesaid reactive groups. In other embodiments, however, they may be attached to reactive groups carried by the aforesaid hydrophilic polymer material, either before or after assembly of the latter to the cationic polymer/nucleic acid complex. For this purpose, the hydrophilic polymer material may conveniently be provided by hydrophilic heterobifunctional or multifinctional polymer molecules that permit in effect the further bioactive agents to be attached to the outside of the steric shield. In many cases, the preferred hydrophilic polymer will be based on copolymers of N-2-hydroxypropylmethacrylamide (BPMA) with activated esters of N-methacryloylated peptides.

In preferred embodiments the molecules of the hydrophilic coating polymer material, such as p(HPMA), will in fact usually be multivalent with a plurality of reactive groups so that, apart from a possible requirement to attach molecules of other bioactive agents, these reactive groups can form a plurality of cross-linkages with the nucleic acid-containing cationic polyelectrolyte polymer core of the complex which may considerably improve the stability of the construct.

The reactive groups carried by the reactive hydrophilic coating polymer may include activated esters (e.g. p-nitrophenyl, p-nitrophenoxy), thiol groups, biotin or aldehyde groups which in some cases may be carried by side chains of the main polymer backbone. Aldehyde groups incorporated in dextran or poly[N-(2-hydroxyethyl)-L-glutamine] (pHEG) may be especially useful for reacting with amino group or hydrazide-bearing cationic polymers.

Where molecules of other bioactive agents are to be attached to the hydrophilic coating polymer, it may be advantageous in some cases to provide the polymer with more than one type of reactive groups having different reactivities. This may facilitate controlling and distinguishing more readily different coupling reactions. Similarly, different kinds of reactive groups having different reactivities may be carried by the cationic polyelectrolyte polymer where different coupling reactions are required.

The reactive group or groups of the cationic polyelectrolyte polymer may be incorporated during the polymerisation or copolymerisation process used in forming the polymer from constituent monomers. Alternatively, an existing cationic polyelectrolyte polymer already having suitable reactive groups, e.g. reactive amino groups as in poly-(L)-lysine, may be used. Or, an existing cationic polyelectrolyte polymer may be modified to introduce the required reactive groups, or to increase the reactivity of an existing reactive group, in a separate preliminary step of the process.

In one useful technique, molecules providing complementary binding groups, such as biotin molecules and avidin or streptavidin molecules, are used. Thus, biotin molecules may be incorporated in the cationic or hydrophilic polymer material, and before use these are linked to avidin or streptavidin molecules providing a complementary binding group attached to appropriate targeting moieties, e.g. site specific antibodies, or other bioactive agents selected by the user. Or, the reverse arrangement with the avidin or streptavidin incorporated in the cationic or hydrophilic polymer material and the biotin attached to the other molecular species may of course be used. The invention also provides a nucleic acid carrier vehicle for in vivo delivery of genes or therapeutic DNA to a patient in carrying out gene therapy or DNA vaccination treatment for example, said carrier vehicle comprising a polyelectrolyte complex of the DNA or other nucleic acid material and cationic polymer material together with one or more molecules of hydrophilic polymer material to provide an outer stabilising steric shield, and comprising also other bioactive molecular species linked either to said cationic polymer or to said hydrophilic polymer material, said complex being constructed in a stepwise process as hereinabove set forth.

The nucleic acid material will usually be DNA although in some cases it could consist of RNA or ribozymes. Antisense nucleic acid may sometimes also be used for certain therapies.

The invention also provides a method of delivering gene DNA material to a patient in carrying out somatic gene therapy treatment, said method comprising packaging the selected DNA as a expression vector in a carrier vehicle constructed as herein described, and administering the polyelectrolyte complex material forming the DNA carrier vehicle to said patient.

From another aspect the invention may be regarded as providing, for delivery of DNA to target calls in biological systems, a synthetic polymer-based carrier vehicle that comprises a polyelectrolyte complex in which a DNA expression vector located in a core portion is electrostatically bound and condensed through self-assembly with a polycationic polymer that, after assembly with said DNA, is coupled or attached via covalent linkages to associated hydrophilic polymer material that provides a stabilising steric shield around the complex.

From yet another aspect the invention may be regarded as consisting in a synthetic polymer-based carrier vehicle for delivery of DNA to target cells in biological systems wherein said carrier vehicle is in the form of a particle consisting of a polyelectrolyte complex comprising a DNA expression vector bound to one or more cationic polymer molecules thereby forming a DNA-containing which is coupled via covalent linkages to one or more associated hydrophilic polymer molecules forming a stabilising and protective steric shield or coating around said DNA-containing complex, and wherein one or more other molecular entities providing bioactive agents or cell receptor targeting moieties are coupled, also via covalent linkages, to said cationic polymer material and/or to the hydrophilic polymer material, with at least some of said covalent linkages being hydrolytically unstable and/or pH sensitive or enzymatically sensitive so as to be biodegradable within the intracellular environment following endocytic uptake and internalisation by a target cell. Alternatively, or in addition, the hydrophilic polymer may include components or linkages in its main chain backbone adapted to be biodegradable within the target cell.

Although the synthetic polymer-based nucleic acid carrier vehicles of the present invention have been designed and developed primarily for in vivo gene therapy, DNA vaccination can be another application and it should be appreciated that in many cases the carrier vehicles will also be suitable for in vitro delivery of DNA to cells, and this is also within the scope of the invention. For example, the carrier vehicles may be used for targeted transfection of cancer cell lines and primary cells in vitro, and this may even be carried out on cells removed from a patient which are subsequently re-introduced as part of an in vivo therapeutic strategy.

In many embodiments the complexes formed with the DNA will include both cationic polymer molecules coupled to a hydrophilic polymer block and cationic polymer molecules coupled to one or more targeting moieties and/or other bioactive molecules, and the stepwise method of construction of this invention may be particularly advantageous. By forming the complex of the DNA with the cationic polymer material first and then adding and incorporating the hydrophilic polymer material in a subsequent assembly step, it is believed that this procedure facilitates the production of more stable and smaller size complexes which is a most important practical feature. Although the presence of a self-assembled coating of synthetic hydrophilic polymer can confer up to 100-fold stabilisation of simple DNA/cationic polymer complexes in the presence of serum proteins, at physiological concentrations of albumin optimal complexes produced in a single assembly step procedure using A-B type linear block copolymers having a cationic polymer block and a hydrophilic polymer block are often still destabilised quite quickly. However, complexes constructed using the 2-stage coating or assembly procedure of this invention are likely to be more stable since there is a reduced risk of hydrophilic polymer being trapped within the structure. It is also possible that by introducing more than one reactive group into the hydrophilic polymer, i.e. where the hydrophilic polymer is multivalent, some cross-linking will occur in the surface coating of the complex as previously mentioned. For example, use of a poly(ethyleneglycol) (pEG) molecule bearing more than one thiol reactive group could react with more than one maleimide group in the cationic polymer core, thereby cross-linking the surface and potentially stabilising the complex. The promotion of such cross-linking by using polymers with multiple reactive groups is a much preferred feature of many embodiments.

There is also an alternative chemistry that can be useful which exploits a differential reactivity of primary amino functions in synthetic cationic polymers and DNA bases. Thus, polyHPMA-based activated esters, e.g. p-aminophenyl esters, should react with primary amino groups on the cationic polymers but not with the DNA. This can therefore allow formation of the DNA/polymer complex, and then attachment of a hydrophilic coating that will simultaneously shield and cross-link the surface for added biological stability, without reacting at all with the DNA if this is desired.

In the DNA carrier vehicles provided by the polyelectrolyte complexes of this invention the DNA expression vector will usually be a plasmid-based expression vector incorporating an appropriate promoter sequence.

As hereinafter described it may sometimes also be useful to use cationic polymers containing a mixture of different types of amino groups, some predominantly charged at neutral pH (e.g. poly(L)lysine) and others subject to significant protonation by the falling pH during endosomal acidification (e.g. L-histidine).

In some embodiments one presently favoured cationic polymer is poly(L)lysine (pLL), preferably with a molecular weight (weight average) greater than 3 kDa but below 25 kDa, and most preforably-in the range 4–20 kDa, in order to provide complexes of a suitable size. However, other polyaminoacids, e.g. poly(L)omithine, can also be suitable, and in some other embodiments non-polypeptide synthetic polymers may be used. The latter can include synthetic polymers containing a primary or tertiary amino group or a quaternary ammonium group, e.g. poly-(trimethylammonioethyl methacrylate chloride) (pTMAEM).

The linkages coupling the molecules attached to the cationic polymer component and/or to the outer coating hydrophilic polymer component may be provided by side chains of the polymer molecules that carry the reactive groups that react to couple the molecules together. Moreover, these linkages may be either stable covalent linkages or, if it is required that the hydrophilic coating and/or attached bioactive agents be shed at the target site to permit release of the DNA, relatively unstable hydrolytic, pH-labile or enzymatically degradable linkages are appropriate. In the latter case these linkages may be susceptible to acid-catalysed cleavage, and it may be arranged so that release or conformational change of attached bioactive molecules can be triggered by the fall in pH within the endosomal or lysosomal compartment containing the complex after it has been internalised within a target cell following endocytosis. This effect can for example facilitate the exposure and activation (or release) of membrane-active fusogenic or membrane-disrupting agents for enabling the DNA to gain access to the cytoplasm of the target cells, and the exposure and activation of nuclear-homing agents, e.g. peptide nuclear-homing agents, for promoting nuclear translocation and expression. Examples of suitable pH-sensitive linkages include cis-aconityl, ortho-ester, bis esters, amides or ester-amides of dimethyl maleimic acid. Alternatively, the linkages may provide a substrate designed for cleavage by cellular enzymes, e.g. they may contain peptide sequences such as GlyPheLeuGly (SEQ ID NO: 1), GlyPheAlaLeu (SEQ ID NO: 2) or hydrolytically unstable groups such as esters incorporated in side chains of the polymer molecules that carry the reactive coupling groups.

It is believed that it will in fact usually be desirable to arrange for the hydrophilic polymer coating of the DNA-containing cationic polymer core to be shed or separate after internalisation in the target cell, either in the endosome or lysosome, in order to open up the structure and prepare for translocation and entry of the DNA into the nucleus. However, instead of relying upon controlled degradation of the linkages between the cationic polymer in the core and the hydrophilic polymer, it is also possible to arrange for the hydrophilic polymer to be synthesised so as to include degradable components, e.g. enzymatically degradable peptide sequences or degradable ester linkages, in the main polymer chain such that the hydrophilic polymer component would be subject to a controlled disintegration within the intracellular environment.

In general, hydrophilic polymer-shielded and/or bioactive agent modified DNA-containing polyelectrolyte complexes constructed in accordance with this invention will be particles having dimensions within a monodisperse size range of less than 100 nm in diameter, generally less than 70 nm in diameter, and possibly approaching an ideal size of 30–40 nm diameter.

For therapeutic use these DNA or other nucleic acid carrier vehicles will usually be made up as pharmaceutical compositions formulated for administration by intravenous injection. However, intra-arterial, intraperitoneal or direct intra-tumoural injection could also be usefuil, and even oral administration may be feasible.

In general, the reactive groups on the polycation and/or hydrophilic polymer for forming the linkages may be selected from thiol, hydroxyl, SPDP (succinimide-3-(2-dithiopyridyl)proprionic acid), maleimide, amine, carboxyl groups, activated esters and complementary biotin/(strept) avidin groups. For promoting the formation of the linkages coupling agents can be used (e.g. glutaraldehyde, EEDQ, carbodiimides).

Activated esters may include for example succinimide, nitrophenyl, pentafluorophenyl or imidazole esters, but in making a selection for therapeutic applications due regard should be given to their toxicity characteristics.

Parameters which are likely to influence the performance and efficiency of the DNA carrier vehicles of the present invention include charge ratio of the polycation to anionic nucleic acid, especially at neutral pH in aqueous solution, and also the overall hydrophilicity/hydrophobicity characteristics of the complex formed by the cationic polymer and DNA core, the molecular weight of the polymer blocks, and the overall size and conformation of the carrier vehicle.

Biologically inert pHPMA and similar methacrylate and methacrylamide based addition polymers represent one preferred category of polymeric material for providing the hydrophilic polymer components of the complexes of this invention.

To adapt biologically inert polymer material such as pHPMA to enable interaction with cell membranes for bringing about transfection, membrane-active lipids, e.g. oleyl, pH-responsive amphipathic peptide helices or constitutively-active amphipathic helices (i.e. not dependent on pH for induction of membrane activity), may be incorporated during synthesis. In addition, there is also a possibility of incorporating agents to provide intemalisation following receptor-binding. A particular example of such an agent is the integrin-binding tripeptide RGD (arginine-glycine-aspartic acid) but other materials, probably also integrin-binding functionalities, could also be used.

The invention also provides new or improved methods for preparing modified cationic polymers incorporating reactive groups, and other features in connection with certain embodiments will become apparent from specific examples hereinafter described in more detail.

BRIEF DESCRIPTION OF THE DRAWINGS

In the accompanying drawings

FIG. 1 is a composite diagram showing an example of the construction and functioning of a DNA vector or delivery vehicle in accordance with the invention and it is made up of FIG. 1A which illustrates a typical set of possible individual components, FIG. 1B which illustrates the assembly thereof following the stepwise procedure of the invention, and FIG. 1C which illustrates stages in the delivery vehicle acting to deliver the DNA therein to a cell in a biological system;

FIG. 2 is a diagram showing the overall reactions involved in constructing DNA delivery vehicles in accordance with Example 7 which is hereinafter described;

FIGS. 7A and 7B is a diagram of the reactions carried out in Example 13.

FIG. 9 is a diagram of the synthesis of 4-nitrophenyl-chlorofornate activated pHEG-pEG.

FIG. 10 is a diagram of the synthesis of pLL-g-pEG via —S— bond

Referring to FIG. 1, the components shown in FIG. 1A comprise a DNA expression vector (A1), a cationic polymer (A2) coupled through a terminal reactive group at an end of the polymer chain to a bioactive component e.g. a fusogenic oleyl molecular group for facilitating membrane penetration, a cationic polymer (A3) provided with a plurality of reactive groups spaced along the polymer chain, a hydrophilic polymer molecule (A4) having a plurality of reactive groups spaced along the polymer chain, and a hydrophilic polymer molecule (A5) having a free reactive group at one end and a biotin molecule attached at the opposite end.

Figure 3:
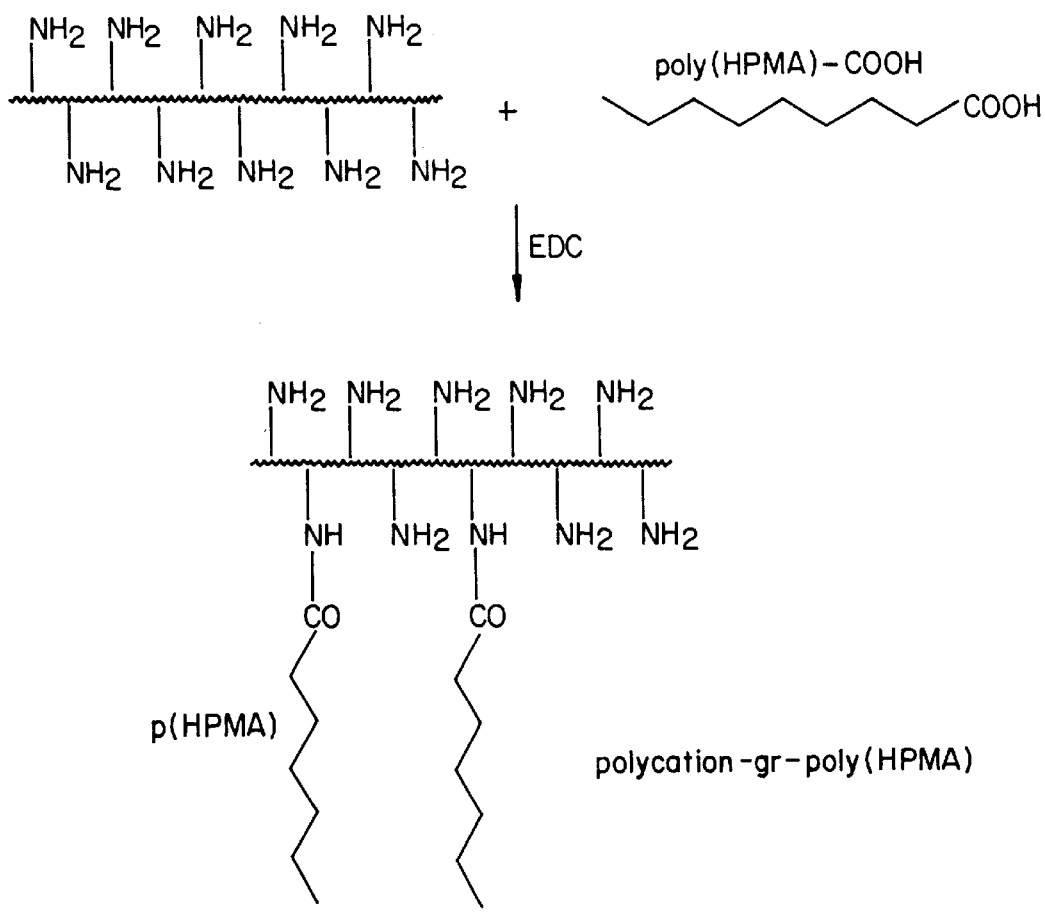
FIG. 3 is a diagram illustrating the synthesis of HPMA.

Stages in the assembly of these components are shown in FIG. 1B, components A1, A2 and A3 first being brought together to form the DNA-containing core of the complex as a result of self-assembly of cationic polymer molecules with the DNA expression vector, molecules of the hydrophilic polymer then being linked to exposed reactive groups of the cationic polymer molecules to form a coating and an outer steric shield for the core. Finally, streptavidin/antibody conjugates are attached to exposed biotin groups carried by molecules of the hydrophilic polymer in order to provide specific cell targeting groups.

In FIG. 1C the pictorial representation shown therein of the main stages involved in the targeted delivery of DNA, using a DNA delivery vehicle assembled as in FIG. 1B, clearly illustrates the initial extravasation and recognition of a target cell, followed by endocytic internalisation, entry into the cytoplasm after shedding the hydrophilic polymer coat, and finally entry of DNA released from the DNA-containing cationic polymer complex into the nucleus.

MORE DETAILED DESCRIPTION OF PREPARATION METHODS AND EXAMPLES

The following examples and descriptions of stages in synthetic routes for preparation of DNA delivery vehicles comprising polyelectrolyte complexes constructed in accordance with the invention, and components thereof, serve to further illustrate the present invention, and dissolve additional important features thereof. They should not, however, be construed in any way as a limitation thereof.

Unless otherwise stated, molecular weight values quoted for polymers are intended to represent weight average values.

In the first example (EXAMPLE 1), the manner of preparation is described of a DNA/polyaminoacid complex formed with a protective hydrophilic polymer coating using a preferred 2-step assembly procedure in accordance with the invention.

Example 1

Preparation by 2-step Assembly Procedure of DNA Delivery Vehicle Complex comprising Cationic Polymer Material and a Coating of Hydrophilic Polymer formed by Polymeric Precursors based on N-2-hydroxypropylmethacrylamide (HPMA) and reactive esters This example relates to the formation of coated particulate complexes made up of DNA, e.g. expression vector plasmid DNA, poly(L)lysine (pLL) and a so-called polymeric precursor composed of HPMA copolymerised with a methacryloylated-oligopeptide(Glycine-Phenylalanine-Leucine-Glycine) para-nitrophenyl ester.

Such methacrylic polymeric precursors provide the hydrophilic polymer material. They will generally have a molecular weight of about 20,000 Da and contain from 4–10 mol % of oligopeptide side chains bearing the activated ester groups (-ONp). The oligopeptide acts as a spacer and may be varied in size, but the tetrapeptide Gly-Phe-Leu-Gly represents one preferred form which is designed for biodegradation by lysosomal cathepsin enzymes (thiol proteinases). A typical structure is shown below:

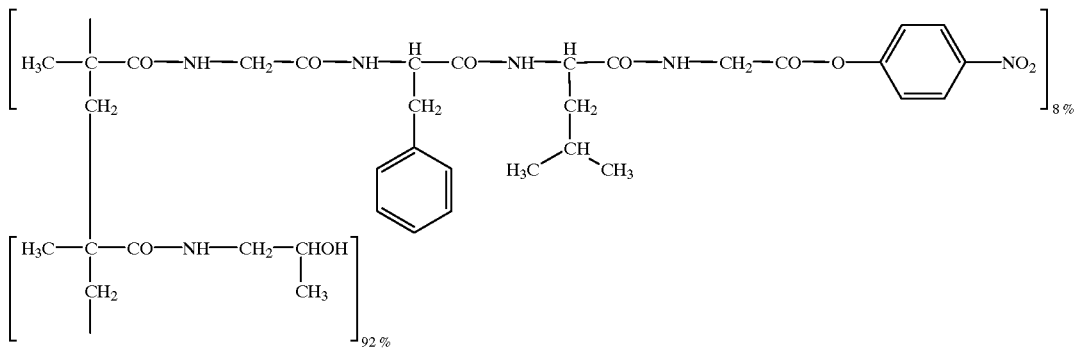

Preparation of methacrylic polymeric precursors as referred to above generally involves a step of copolymerisation of HPMA with the p-nitrophenyl ester of the N-methacryloylated peptide concerned, and in the "polymeric precursor" so formed the terminal p-nitrophenoxy groups of the peptide side-chains provide convenient leaving groups for subsequent addition reactions with reactive amino or other functional groups of the cationic polymer molecules or of other molecular entities such as targeting moieties that it may be desired to incorporate. The synthesis of p-nitrophenyl esters of N-methacryloylated oligopeptides and their copolymers with HPMA is well documented in the literature, especially in articles or papers relating to synthetic polymer drug delivery agents, as for example P. Rejmanova et al "Aminolyses of Monomeric and Polymeric 4-Nitrophenyl Esters of N-Methacryloylamino Acids", (1977), *Makromol. Chem.* 178, 2159–2168, Subr. V, et al, "Polymers Containing Enzymatically Degradable Bonds", (1992), *Journal of Controlled Release*, 18, No. 2, pp.123–132 and Ulbrich, K. et al, "Polymeric Conjugates of Drugs and Antibodies for Site-Specific Drug-Delivery" *Macromolecular Symposia*, (1996), 103, pp. 177–192. See also EP-A-0187547 of which the content is incorporated herein by reference.

The preparation of hydrophilic poly(HPMA) polymers having side chains bearing reactive p-nitrophenyl esters or reactive p-nitrophenoxy groups is hereinafter more particularly described in Examples 3 and 4.

It is incidentally also possible for constructing the hydrophilic polymer to use polymeric precursors of HPMA copolymerised with N-methacryloylated oligopeptides in which the peptide side chains terminate in carboxyl groups instead of p-nitrophenyl ester groups, prepared as described in EP-A-0187547. In the presence of suitable catalysts (again see EP-A-0187547) the carboxyl groups will bind to primary amino groups on the polycation, as with nitrophenyl esters. However, an additional possibility also arises in that the carboxyl groups may bind to reactive alcohol groups in the DNA-polycation complex (potentially either on the DNA and/or the cationic polymer), forming ester groups. In that event such ester groups may be subsequently broken down through acid-catalysed or hydrolytic degradation.

In the present example the cationic polymer/DNA complex was initially formed by gently adding an aqueous solution of the poly(L-lysine) to a DNA solution in water, at a DNA concentration of 40 μg/ml and a final cation:anion charge ratio of 2.0. In general, this charge ratio should lie within the range of 0.7 to 4.2, at least in neutral solution (pH 7). The reaction mixture was then allowed to stand for at least 30 min at room temperature to permit complete self-assembly of complexes. The pH of the solution was then raised to approximately neutral using an equal volume of 100 mM borate solution. It is important that the solution does not contain nucleophilic groups such as amines (e.g. Tris buffer) which might react with the hydrophilic polymers in the next stage. It is also important that the solution should not become too alkaline (e.g. pH not >8.0) as this will promote unwanted hydrolysis of activated ester groups in the next stage.

In the next stage, the hydrophilic polymer (polymeric precursor) bearing reactive ester groups was added to the mixture with gentle mixing (200 μg/m). The reaction between the -ONp ester groups and the primary amino functions of the cationic polymer was monitored spectrophotometrically, either by measuring decreasing concentration of the esters or by monitoring appearance of free paranitrophenol. After 2 h the pH was raised to 8.0, accelerating the rate of both aminolysis and hydrolysis, and the complexes formed were ready for use 30 min later.

The reactive esters did not appear to react with DNA, but reacted rapidly under these conditions with unprotonated amino groups of the cationic polymers.

Optimal reaction conditions include gentle mixing (but not vortexing), either in borate solution or in water/NaOH at pH 7.0–7.6, a temperature of 15–37° C., and a maximal DNA concentration of 80 μg/ml to avoid flocculation. This maximal concentration of DNA depends on the hydrophilicity of the structure of the cationic polymer, but for 25 kDa poly(L-lysine), the optimal concentration is in the range 20–50 μg/ml.

The reaction is preferably carried out using a molar ratio of amines to activated esters within the range 0.7–4.0.

In some instances the pH may be gradually raised during the reaction, either by addition of sodium hydroxide or a higher pH buffer, up to about pH 8.0. This promotes reactivity of the poly(L-lysine) primary amino groups, but must be regulated carefully as it also accelerates the rate of ester hydrolysis.

The reaction may be terminated either by raising the pH to 8.5, promoting rapid ester hydrolysis as mentioned above, or by addition of low molecular weight reactive amines, e.g. aminopropanol or 4-aminobutan-1-ol.

Typical particles produced as described in this example, containing expression vector DNA, low molecular weight poly(L-lysine) (molecular weight 4–25 kDa approx.) and hydrophilic polymer material provided by the polymeric precursor of the kind referred to, are discrete and have a small overall size (30–50 nm diameter, as determined by atomic force microscopy).

Particles formed and coated in this way also show improved stability to proteins. For example, simple poly(L-lysine)/DNA complexes formed at a charge ratio (cation:anion) >1.0 are subject to binding and destabilisation by albumin. This results in restoration of ethidium bromide/DNA fluorescence, and the existence of an albumin/poly(L-lysine)/DNA ternary complex can be demonstrated using agarose electrophoresis, where the ternary complex remains at the origin and fluoresces. Disruption by albumin can be measured in a fluorimeter by the restoration of ethidium bromide/DNA fluorescence, and hydrophilic polymer coated complexes have been found to be in general at least 100 times more stable than uncoated particles. Moreover they retain integrity and do not fluoresce even when incubated in the presence of physiological serum concentrations of albumin.

It has also been found that the coated complexes are relatively stable and easy to handle, and they can be purified by column chromatography (e.g. SEPHAROSE 4B-CL) or by density gradient centrifuigation.

If desired, the coated complexes can be formed using $^{32}$P-labelled linearised expression vector DNA to permit determination of DNA distribution following injection in vivo.

Synthesis of the reactive hydrophilic polymer used in the above example which contains tetrapeptide-paranitrophenyl esters, has already been referred to. Careful selection of the reactive hydrophilic coating polymer can significantly affect the properties of the resulting coated complexes. For example, use of polymers having simple oligopeptide-nitrophenyl ester reactive side chains leads to aminolytic reaction with uncharged amino groups of the cationic polymer with release of p-nitrophenol, but there is also a significant component of hydrolysis. The hydrolytic product is a free carboxylic acid at the terminal amino acid, and hence such coated complexes are often found to possess strongly negative surface charges (e.g. zeta potential of −25 mV for 2:1 charge ratio pLL/DNA complexes, containing 20 μg/ml DNA and 200 μg/ml reactive ester). Alternative chemistry, for example using carbonate esters of paranitrophenol yield the same products on aminolysis, with release of carbon dioxide, but produce hydroxyl groups following hydrolysis. The measured zeta potential of the resulting coated particles is generally very close to zero, although it can be influenced by the composition of the polyelectrolyte core of the complex.

Several other reactive hydrophilic polymers can be used to achieve stabilisation of pre-formed polycation/DNA complexes. These include reactive esters based on other polymer backbones, such as poly-N5-(2-hydroxyethyl)-L-glutamine (pHEG), or reactive polymers containing backbones composed primarily of blocks of poly(ethylene glycol) joined end-to-end by oligopeptide or other biodegradable sequences bearing pendant reactive esters. Careful selection of the structure of these molecules can tailor them for degradation by specific enzymes, in specific locations, or for hydrolytic or acid-catalysed hydrolytic degradation. The synthesis of some of these materials is described in later examples, and they make particularly effective agents for stabilisation of polyelectrolyte DNA complexes, using the same protocol as described above. Reactive hydrophilic polymer material based on poly-N-(2-hydroxyethyl-L-glutamine) (pHEG), containing reactive ONp carbonate esters with no amino acid spacer, can be produced by reaction of pHEG with chloroformate and is known to be readily biodegradable.

Coated complexes formed with a net strong negative surface charge are subject to rapid scavenging by phagocytic cells, notably Kupffer cells, following intravenous administration. Complexes bearing net positive charges are prone to accumulation in capillary beds, notably the pulmonary capillaries.

Accordingly, the best surface charge for achieving prolonged plasma circulation is neutral or slightly negative.

As will be appreciated, other bioactive molecules, such as targeting groups or additional shielding molecules, may be attached to the hydrophilic polymer precursor. In an example described below (EXAMPLE 6), the targeting agent transferrin has been incorporated by simple aminolysis or following oxidation of its carbohydrate component.

Example 2

Self-assembly of poly(L-lysine) with DNA and bioactive oligopeptides Prior to Coating with Reactive Hydrophilic Polymers In this example poly(L-lysine), molecular weight 22 kDa. 40 μg/ml, was allowed to self assemble into complexes with expression vector DNA at a charge ratio of about 4 in water. Complexes were then diluted into 50 mM borate solution pH 7.4 and a 28-mer fusogenic oligopeptide known as M7-GSGC (obtained from Severn Biochemical Ltd, U.K.) was added to a final concentration of 10 μM. INF7-GSGC is thought to promote end-osome/lysosome-to-cytoplasm transfer of gene complexes (see Wolfert et al (1996), *Human Gene Therapy*, 7, 2123–2133). After 1 h the complexes were reacted with pHEG-ONp (final concentration 200 μg/ml) to provide a hydrophilic polymer coating and surface stabilisation. They were then found to be stable to potential disruption by albumin even at physiological serum concentrations, indicating that the coating reaction proceeded efficiently.

A similar experiment has also been performed using a reactive ester based on alternating polyethylene glycol segments and peptide blocks bearing pendant reactive paranitrophenyl esters. Very efficient stabilisation to albumin disruption has been determined, using the reactive polymer at concentrations of 100, 200 and 300 μg/ml, although increasing stability was achieved with increasing amount of polymer over this range.

Example 3

Synthesis of poly(HPMA) with oligopeptide Side Chains Bearing Reactive Para-Nitrophenyl Esters 2 g HPMA, 200 mg of MA(methacryloyl)-GlyPheLeuGly-ONp and 132 mg AIBN were dissolved in 18 g (22.8 ml) acetone, placed into a polymerization ampoule and bubbled through with nitrogen. The ampoule was then sealed and kept in a bath at 50° C. for 20 hours. The polymer product was isolated by filtration, washed three times with 50 ml of mixture of acetone-diethylether (3:1). It was then washed with pure diethylether and dried in vacuo. The content of ONp groups was estimated using UV absorption at 274 nm, extinction coefficient 9500 l/mol.cm in DMSO.

The content of the monomer MA-X-ONp (X=oligopeptide) can be varied in the range 3–9 mol % of co-monomer in the polymerization mixture, depending on the amount of side chains required in the final product. OSu esters can be prepared similarly using the monomer MA-X-OSu.

Example 4

Synthesis of poly(HPMA) with oligopeptide Side Chains Bearing Reactive Para-Nitrophenoxy Groups In this example, pure poly(BPMA) was modified by reaction with p-nitrophenylchloroformate to modify the secondary hydroxyl groups to form -OCOONp.

1 g of poly(HPMA) was dissolved in 8 ml dimethylformamide and 2 ml pyridine were added under stirring. 0.5 g of p-nitrophenyl chloroformate was added slowly under intensive stirring, the solution was stirred at 45° C. for 1 h and, after cooling to room temperature, polymer containing reactive p-nitrophenoxy groups was isolated by precipitation into a mixture of acetone-diethylether 2:1. The polymer product was washed with two portions of ether and dried under vacuo.

This material was then used as a reactive polymeric ester, stabilising complexes as described in Example 1, but yielding complexes which are activated by acid-catalysed ester hydrolysis. Such coated complexes are particularly useful where the complex is required to undergo activation within the low pH environment of the endosome after uptake by target cells.

Example 5
Synthesis of Hydrophilic Block Copolymers Bearing Reactive Esters, and Designed For ph-Catalysed Hydrolytic Instability in the Polymer Backbone This example is selected to demonstrate the possibility of preparing hydrophilic reactive polymers which are capable of stabilising DNA-containing complexes, and which are themselves susceptible to acid-catalysed hydrolysis. Such a system permits disintegration of the coating molecule within the endosome, releasing the DNA to begin a journey into the cytoplasm and thence to the nucleus.

This coating polymer is based on polyethylene glycol (pEG) blocks joined end-to-end by hydrolytically unstable linkages. HO-pEG-OH, dissolved in methylene chloride, was first reacted with maleic anhydride to yield terminal carboxylic groups. These end groups were then modified by dicyclo-hexylcarbodiimide (DCCI)-catalysed reaction with N-hydroxysuccinimide (NHS) to yield NHS ester end groups. The modified pEG esters were then linked together by reaction with lysine benzylester, with subsequent removal of the protecting benzylester group (using hydrogen on Pd-black) to expose the carboxyl termini of the lysine residues. Finally the reactive ONp esters were introduced by reaction of the lysine carboxylic groups with p-nitrophenol (in methylene chloride) in the presence of DCCI.

The resulting polymer, containing blocks of pEG linked end to end in a hydrolytically-unstable polymer backbone, and with pendant ONp groups, can then be used as described above for covalent stabilisation of DNA complexes with cationic polymers containing primary amino groups. Again this material has the feature of undergoing rapid hydrolytic degradation in the presence of acid, and is suitable for stabilisation of complexes which require liberation/activation of DNA within the endosomal compartment. The polymer structure can be depicted as shown below:

at a charge ratio 2:1 cationic excess). To inhibit precipitation the polycation was added into the DNA solution. The mixture was left for 30 min to stabilise, and then was diluted 1:1 with 100 mM borate solution (pH 7.4, final concentration 50 mM). Fusogenic peptide known as INF7-SGSC (Wolfert et al., 1996) was then added in 10 μl DMSO, to a final concentration of 10 μM. The solution was kept cool to avoid precipitation. After 30 min 800 μg reactive hydrophilic polymer (PHPMA bearing Gly-Phe-Leu-Gly-paranitrophenyl esters, (SEQ ID NO: 1) 8 mol %, as from Example 1) was added (final concentration 200 μg/ml). The reaction was allowed to proceed for 3 min, before addition of holotransferrin (500 μg), and the reaction was then allowed to continue for 2 hours, after which time the pH was increased to pH 8.0 using sodium hydroxide. The complexes were allowed to stand for a further 30 min, and were then purified and sterilised by gel permeation chromatography (SEPHAROSE 4B-CL).

As an alternative the above reaction may be performed in an automatic titration apparatus (e.g. a pH-STAT from Radiometer) maintained at 16° C. and programmed to manipulate the pH conditions as described.

Complexes were then incubated in serum-free medium with transferrin receptor-positive K562 cells, final DNA concentration 4 μg/ml, for 4 h and cells were then reincubated in tissue culture medium containing 10% serum for a further 44h prior to measurement of β-galactosidase reporter gene expression using a commercial Galactolight™ luminescence kit. Transferrin-targeted complexes were found to mediate significantly higher gene expression than non-targeted complexes, and this transfection activity could be inhibited by the addition of excess competing free transferrin. When incubated with transferrin receptor-negative 293 cells, however, these transferrin-targeted complexes gave no transfection activity.

Despite this demonstration of transferrin-targeted gene expression using coated complexes, the result was rather unexpected since the complexes possess no intrinsic mechanism for leaving the endosome/lysosome system and entering the cytoplasm. In addition, this example demonstrates the ability of cells to remove hydrophilic polymer coatings from the complexes and liberate the DNA, since direct injection of coated complexes into the nucleus of xenopus oocytes is known to give no measurable gene expression.

Example 6A
Construction of Transferrin Targeted 2-Stage DNA Complexes Using Carbohydrate Oxidation Poly(L-lysine)/DNA complexes were prepared at a charge ratio of 4, with or without the addition of INF7-SGSC, and

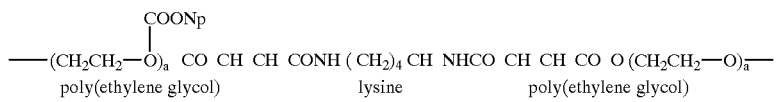

As an alternative, succinic esters can be readily substituted for maleic esters.

Example 6
Construction of Transferrin-Targeted 2-Stage DNA Complexes Using Aminolysis A DNA reporter construct (containing β galactosidase gene under the regulation of the cytomegalovirus immediate early gene promoter, encoded within a pUC19 vector) (final concentration 40 μg/ml, 2 ml) was allowed to self-assemble in water with poly(L-lysine) (22 kDa molecular weight, used were coated with a reactive hydrophilic polymer as described above. In contrast to Example 6, however, no transferrin was used and the coating reaction was terminated by the addition of a 20-fold molar excess of diaminoethylene. This resulted in the incorporation of amino groups onto the surface of the coated complexes via the remaining unreacted ONp ester groups. The amino group-bearing coated complexes were purified from free diamine and polymer by gel filtration on SEPHAROSE 4B-CL with distilled water as eluent.

For the oxidation of the transferrin carbohydrate chain, 10 mg transferrin (0.13 μmol) was dissolved in 0.45 ml of sodium acetate buffer (pH 5.0, 30 mM) and chilled to 0° C. Freshly dissolved sodium periodate (50 μl of a 10 mg/ml solution) was added and the reaction was performed for 90 min at 0° C. in the dark. The oxidised transferrin was purified by gel filtration on prepacked PD10 columns (Pharmacia) and the presence of aldehyde groups was demonstrated using the anisaldehyde test. The oxidised transferrin was kept at pH 5.0 to prevent autoreaction.

For linkage of the oxidised transferrin to the amino function-bearing coated complexes, an appropriate amount of oxidised transferrin was added to purified coated complexes and the pH was adjusted to 7.4. The mixture was left for 1–2 hrs to permit formation of Schiffs base type covalent linkages. The Schiffs bases were subsequently stabilised by reduction for a minimum of 1 hr using an excess of cyanoborohydride. Finally the complexes were purified from unincorporated transferrin and cyanoborohydride and sterilised by gel filtration on SEPHAROSE 4B-CL or equivalent with PBS pH 7.4 as eluent.

In a typical reaction, 246 nmol DNA (bases) are condensed with 492 nmol polycation (amino groups), coated with 800 μg HPMA-based hydrophilic polymer containing 264 nmol amine-reactive ONp esters. Approximately 50 nmol of the latter react with diaminopropanol to yield amino groups used to bind approximately 25 nmol oxidised transferrin. This relates to about 100 molecules of transferrin per 6 kb expression vector DNA molecule. Biological activity was demonstrated as described above.

Example 6B

Construction of Transferrin Targeted 2-Stage DNA Complexes Using a Heterobifunctional Crosslinker This procedure involved production of polymer-coated polycation/DNA complexes bearing SH groups and their conjugation with SH-reactive transferrin molecules.

Poly(L-lysine)-condensed DNA complexes with or without INF7-SGSC were prepared at 40 μg/ml DNA as described above. Cysteamine (2-aminoethane thiol) was reacted with the pHPMA-based reactive coating polymer at different ratios (from 2 to 25% equivalent to the reactive esters) prior to addition to the pLL/DNA complexes. This reaction was carried out in a pH-STAT (Radiometer) at pH 7.4 and 16° C., as follows:

An appropriate amount of the precursor form of the hydrophilic coating material (for example 400 μg/ml of a pHPMA-based copolymer with 8 mol % activated ester group) was dissolved in water and the desired amount of cysteamine was added. The reaction of the polymer precursor with cysteamine was started by raising the pH to 7.4. The reaction is very rapid and is essentially complete after 3 min. The modified polymer precursor was stored at pH 6.0 to prevent unwanted hydrolysis.

An equal volume of the preformed pLL/DNA complexes was then added to the modified polymer precursor to give a DNA concentration of 201 μg/ml. The reaction of the coating material with the amino groups of the DNA condensing polycation was initiated by increasing the pH to 7.4, and allowed to proceed for 2 hrs. Unreacted ONp ester groups were then reacted with an excess of aminopropanol.

Sulphide-reactive transferrin was prepared as follows: Transferrin was dissolved in water at 25 ng/ml. Between 1–2 molar-equivalents of succinimidopyridyldithiopropionate (SPDP) was added (for 1 ml of 25 mg/ml (transferrin, around 201 μl of a 10 mg/ml SPDP solution would be used). The mixture was left for 1 hr at room temperature before being subject to gel filtration using a PD10 column.

The sulphide-reactive pyridyldithiopriopionate-transferrin (PDP-Tf) was now reacted onto sulphide-bearing coated DNA complexes. This was achieved by adding an appropriate amount of the PDP-Tf to a solution of coated complexes prepared as described above under neutral conditions. The exchange reaction was allowed to proceed overnight.

All reactions were carried out in an oxygen-free atmosphere using degassed solutions to prevent formation of disulphide bonds by the coating polymer, potentially leading to the formation of aggregates. For the same reason a molar excess of sulphide-reactive transferrin over sulphide groups of the coating material was used. After completion of all reactions. the complexes were purified from non-incorporated materials and reaction by-products and sterilised by aseptic gel filtration on SEPHAROSE 4B-CL or other suitable matrices. Phosphate buffered saline was used as the eluent. Biological activity was demonstrated as described above.

The next example (Example 7) describes the formation of complexes of DNA with polyamines combined with polyethylene glycol (pEG) grafted thereto via a labile disulphide bond. These complexes are obtained by forming a complex of DNA with a partially modified form of the polyamine, followed by grafting of polyethylene glycol via a disulfide bond.

Example 7

Formation of a Complex of DNA with a Partially Modified Polyamine Followed by Grafting of Polyethylene Glycol Via a Disulfide Bond (a) General Scheme The polyamine (poly-L-lysine, polyallylamine, polyethyleneimine, etc.) is partially modified to introduce side chains with reactive terminal groups by reacting with N-succinimidyl 3-(2-pyridyldithio)propionate (SPDP) and is then mixed with DNA giving a polyelectrolyte complex. The addition of α-methoxy-ω-thiol-polyethyleneoxide (pEG-SH) then leads to grafting of hydrophilic pEG blocks onto the polyamine backbone via labile S—S bonds.

Details of the preparation of a complex of DNA with a partially modified polyamine, in this example poly-L-lysine, followed by grafting of polyethylene glycol are given below. The overall scheme is illustrated in the diagram of FIG. 2.

(b) 1st Stage—Modification of the polyamine with N-succinimidyl 3-(2-pyridyldithio)propionate (SPDP);

Poly-L-lysine (pLL) (100 mg, MW=20,000) was dissolved in 30 ml of phosphate buffer, pH 7, containing 0.1M sodium chloride. SPDP (15 mg) was dissolved in 3 ml ethyl alcohol and was added to the solution of pLL. After 2 hours reaction at room temperature the product-was dialyzed against 0.01N hydrochloric acid and was then purified by preparative size exclusion chromatography using Sephadex G-25™. The product could then be isolated by lyophilization.

The degree of substitution (5 mol %) was conveniently determined by UV spectroscopy after reacting the polymer with dithiothreitol (DTT). The concentration of the released pyridine-2-thione, determined by its absorption at 343 nm, is equivalent to the concentration of the pyridyldithio end groups.

(c) 2nd Stage—Formation of a Complex of DNA with the Partially Modified pLL Containing a Disulfide Bond A solution of 123mg DNA (Calf thymus, Sigma Chemical Co., average molecular size 8 kb) in 6 ml water (oxygen-free), was mixed with a solution of 50 mg of the modified pLL in 4 ml water (oxygen-free) at pH 7.4 (charge ratio pLL/DNA of 1.0). After 1 hour at room temperature the formation of the complex was confirmed by agarose gel electrophoresis, atomic force microscopy, and photon correlation spectroscopy.

(d) 3rd Stage—Reaction of the DNA/Modified pLL Complex with pEG-SH

The complex formed in the 2nd stage above was mixed under argon with a solution of 100 mg pEG-SH in 3 ml phosphate buffer, pH 7.4 (oxygen-free). The reaction was carried out at room temperature for 4 hours. The pEG-containing complex produced was examined by agarose gel electrophoresis, atomic force microscopy, and photon correlation spectroscopy. The grafting of pEG (5 mol %) via disulfide bonds was confirmed by UV spectroscopy (absorption at 412 nm) after reaction with DTT, followed by quantitative determination of the pEG-SH released using 5,5'-dithiobis(2-nitrobenzoic acid) (DTNB).

By using a polyethylene glycol bearing reactive thiol end groups cross-linking with the cationic polyamine polymer may be achieved at different locations, thereby increasing the stability of the coated complexes.

Example 8
Synthesis of Cationic Polymers based on Acrylic or Methacrylic Monomers Having Reactive Amino or Alkyl Amino Functional Groups The cationic polymer material required for constructing the DNA delivery vehicles in accordance with the invention, instead of being based on polyaminoacids as in the preceding Examples, may be based on the polymerization of acrylic or methacrylic monomers producing, for example, cationic polymers or copolymers containing methacryloyl-2-amidoethylene diamine, methacryloyl glycyl-2-amidoethylene diamine, methacryloyl diglycyl-2-amidoethylene diamine, methacryloyl-6-hexamethylene diamine, methacryloyl glycyl-6-hexamethylene diamine, or methacryloyl diglycyl-6-hexamethylene diamine.

This will be further described by way of example with reference to cationic polymers or polymer blocks built up from acrylic or methacrylic monomers terminating in a protected amino or alkyl (preferably $C_{1-6}$ alkyl, more preferably $C_{1-4}$ alkyl) amino group that can eventually be converted into a cationic ionised form or into an activated terminal amino group, e.g. for coupling to a hydrophilic polymer. Specific examples of such monomers, labelled (M1), (M2), (M3), (M4), (M5) and (M6), are depicted below, compounds (M1), (M2) and (M3) each including a peptide chain terminating in a tertiary-butyl carbonyl (BOC)-protected amino group.

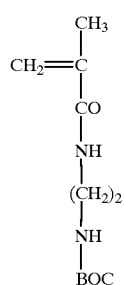

(M1)

-continued

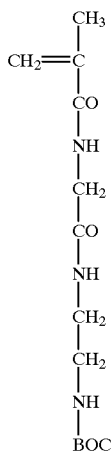

(M2)

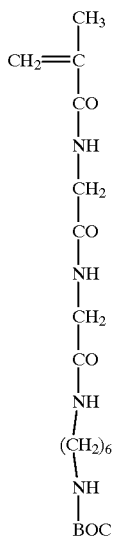

(M3)

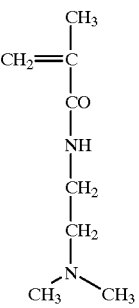

(M4)

-continued

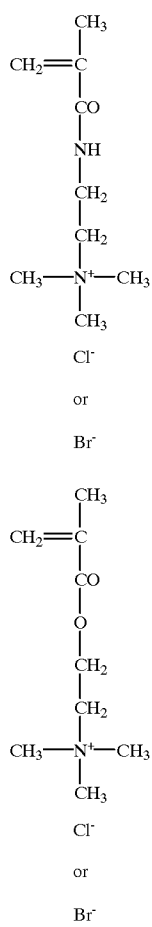

(M5)

(M6)

Preparation of these monomers from commercially available starting materials is illustrated by the following examples.

8.1.1 Synthesis of Ma—NH—(CH2)$_2$—NH-BOC (Compound M1)

8.1.1.1 1st Stage—Preparation of N-BOC-1,2-diaminoethane

A solution of di-tert.-butyl dicarbonate (2.45 g, 0.011 mol) in dioxane (30 ml) was added over a period of 2½ hours to a solution of 1,2-diamino-ethane (5.25 g, 0.087 mol) in dioxane (30 ml). The mixture was stirred for 22 hours at room temperature. The dioxane was evaporated in vacuo and then 50 ml of water was added. The insoluble bis-substituted diamine was removed by filtration. The filtrate was extracted three times with methylene chloride (150 ml). The methylene chloride layer was separated, dried over Na$_2$SO$_4$ and evaporated. The yield was 1.29 g (72%) of N-BOC-1,2-diaminoethane, BOC-NH—(CH$_2$)$_2$-NH$_2$, obtained as an oily product. This oily product was then used in the next stage for the synthesis of the target compound Ma—NH—(CH$_2$)$_2$—NH-BOC without further purification.

8.1.1.2 Final Stage

N-BOC-1,2-diaminoethane (1 g, 0.00625 mol) and triethylaiiiine (Et$_3$N, 5.5 ml) were dissolved in 50 ml of freshly distilled chloroform. The mixture was cooled to −5° C. and methacryloyl chloride (0.68 g, 0.0065 mol) was added dropwise during 3 hours. The reaction mixture was extracted four times with 20 ml of water and then a chloroform layer was dried with Na$_2$SO$_4$. Chloroform was evaporated and after trituration in diethyl ether a yellow crude product was obtained. This product was purified by recrystallisation from the benzene-hexane mixture. Yield was 1.2 g (81%). Melting point: 73–76° C.

8.1.2 Synthesis of Ma-Gly-NH—(CH$_2$)$_2$—NH-BOC (Compound M2)

8.1.2.1 1st Stage—Preparation of Ma-Gly-ONp

For this synthesis, N-methacryloyl glycine p-nitrophenyl ester (Ma-Gly-ONp) was prepared by Schotten-Baumann reaction of freshly distilled methacryloyl chloride with glycine in alkaline aqueous solution. Esterification with p-nitrophenol was performed in the presence of dicyclohexylcarbodiimide.

8.1.2.2 Final Stage

BOC-NH—(CH$_2$)$_2$—NH$_2$ (1.1 g, 0.0068 mol), prepared as in 1.1.1 above, was dissolved in 2 ml of DMSO. Ma-Gly-ONp from 1.2.1 (1.6 g, 0.0061 mol) was dissolved in 3.5 ml of DMSO and added dropwise to the solution of the amine. The reaction mixture was then stirred for 2 hours at laboratory temperature. The DMSO was evaporated in vacuo (maximum temperature 55° C.) and an oily residue was dissolved in 50 ml of chloroform. An organic layer was extracted 3 times with 20 ml of distilled water and was dried over Na$_2$SO$_4$. The chloroform was evaporated, and the product Ma-Gly-NH—(CH$_2$)$_2$—NH-BOC was crystallised from ethyl acetate. Melting point: 136–38° C.

8.1.3 Synthesis of Ma-GlyGly-NH—(CH$_2$)$_6$—NH-BOC (Compound M3)

8.1.3.1 1st Stage—Preparation of Ma-GlyGly-ONp

For this synthesis, N-methacryloyl glycylglycine p-nitrophenyl ester (Ma-GlyGly-ONp) was prepared by Schotten-Baumann reaction of freshly distilled methacrvloyl chloride with glycylglycine in alkaline aqueous solution. Esterification with p-nitrophenol was performed in the presence of dicyclohexylcarbodiimide.

8.1.3.2 Final Stage

Ma-GlyGly-ONp (3 g, 0.0093 mol) and commercially obtained N-BOC-1,6-diamino-hexane hydrochloride were dissolved in 15 ml of N,N-dimethylformamide (DME). Triethylamine (1.3 ml) was added in three portions and the reaction mixture was stirred for 24 hours at room temperature. The precipitated triethylamine hydrochloride was filtered off and the filtrate was evaporated in vacuo to dryness. The crude product was dissolved in chloroform and extracted three times with 15 ml of water. An organic layer was dried with Na$_2$SO$_4$ and evaporated in vacuo. The product was crystallised from a mixture of chloroform-diethyl ether. Melting point: 122–124° C. Yield was 1.98 g (54%).

8.1.4 Synthesis of Dimethylaminoethylmethacrylamide (DMAEM) (Compound M4)

N,N-dimethyl ethylenediamine (8.22 g, 0.093 mol) was diluted with 30 ml of dichloromethane and the solution was cooled to −15° C. Freshly distilled methacryloyl chloride (5.0 g, 0.047 mol) was then added dropwise during 2 hours. Precipitated N,N-dimethylethylenediamine hydrochloride was filtered off and dichloromethane was evaporated from the reaction mixture. The product was then purified by distillation at reduced pressure.

The corresponding ester compound, dimethylammonioethyl-methacrylate may be prepared in a similar way using N,N-dimethylaminoethyl alcohol instead of the N,N-dimethyl ethylenediamine. A similar process can also be used to prepare higher alkyl amino compounds, e.g. diethylamnmonioethylmethacrylamide/methacrylate.

8.1.5 Synthesis of 2-(Trimethylammonio)ethyl methacrylamide chloride (TMAEM.Cl$^-$) (Compound M5)

2-(Trimethylammonio)ethylmethacrylamide chloride (TMAEM.Cl⁻) was prepared by quatemization of 75 g dimethylaminoethylmethacrylamide (DMAEM), prepared as in 8.1.4 above, with gaseous methyl chloride in 200 ml acetone in the presence of 5 ml N,N-dimethylformamide at room temperature. Melting point 174° C. The corresponding bromide salt may be prepared in the same way. Also, higher alkyl amino compounds, e.g. triethylam-monio, may be prepared using the appropriate dialkylammonio compound.

8.1.6 Synthesis of 2-(Trimethylammonio)ethyl methacrylate chloride
(TMAEM.Cl⁻) (Compound M6)

The analogous compound 2-(Trimethylammonio) ethylmethacryiate chloride (TMAEM.Cl⁻) can also be prepared in the same way by quaternization of dimethylaminoethylmethacrylate (DMAEM), synthesized as referred to in 8.1.4 above, with gaseous methyl chloride in acetone in the presence of N,N-dimethylformamide at room temperature. Again, the corresponding bromide salt and/or a higher alkyl amino compound may be prepared in a similar manner, as indicated under 8.1.5 above.

Characterisation of Monomers

Monomers referred to above have been characterised by determination of the melting point and by an elemental analysis. The characterisation of the monomers is summarised in Table 1.

TABLE 1

Characterisation of monomers

| Sample | Structure of monomer | Melting point °C. | elemental analysis calculated/ found | | | |
|---|---|---|---|---|---|---|
| | | | C | H | N | Cl |
| 1 | Ma-NH(CH₂)₂NH-BOC | 73–76 | 57.87 | 8.83 | 12.27 | |
| | | | 57.64 | 9.08 | 12.29 | |
| 2 | Ma-Gly-NH(CH₂)₂NH-BOC | 136–38 | 54.72 | 8.12 | 14.73 | |
| | | | 54.73 | 8.18 | 14.65 | |
| 3 | Ma-(Gly)₂-NH(CH₂)₆NH-BOC | 122–24 | 57.27 | 8.60 | 14.06 | |
| | | | 57.43 | 8.84 | 14.00 | |
| 4 | DMAEM | — | 61.54 | 10.26 | 17.95 | |
| | | | 61.22 | 10.76 | 17.65 | |
| 5 | TMAEM.Cl⁻ | 174 | 52.45 | 8.74 | 6.78 | 17.09 |
| | | | 52.20 | 8.83 | 6.72 | 16.83 |

8.2 Synthesis of Cationic Polymers

By way of example of the use of the above-described monomers to synthesize cationic polymers for building DNA carrier vehicles in accordance with the invention there is next described the synthesis of cationic polymers with carboxylic end groups and the synthesis of cationic polymers with an amino end group.

8.2.1 Synthesis of Cationic Polymers with Carboxylic End Groups

A monomer selected from one of the compounds (M1), (M2) and (M3) prepared as described above was dissolved in methanol to form a solution containing 7–30 wt % of monomer. Commercially obtained (Fluka AG) 4,4'-azo-bis (4-cyanovaleric acid) was then used as an initiator; the concentration was 0.1–2 wt % relative to the polymerisation mixture. To facilitate polymer radiolabelling, N-methacryloyl tyrosinamide (1 mol % relative to monomer) may be added, this being prepared by the reaction of methacryloyl chloride with tyrosinamide in aqueous solution. The solution was introduced into an ampule and bubbled through with nitrogen. The ampule was sealed and polymerisation was carried out at a temperature ranging from 50 to 60° C. for 24 hours. The polymer was precipitated into diethyl ether. The precipitated polymer was filtered off, washed with diethyl ether and dried in vacua. The butyl carbonyl (BOC) protection group of the primary amino groups in the side chains of the cationic polymer was then removed by addition of trifluoracetic acid to a methanolic solution of the polymer. The deprotected polymer was diluted with methanol, evaporated in vacuo to remove the excess of trifluoracetic acid, and precipitated from methanol into diethyl ether. Again, the precipitated polymer was filtered off, washed with diethyl ether and dried in vacuo.

The same procedure was applicable to each of the monomers (M1), (M2) and (M3).

8.2.2 Synthesis of Cationic Polymers with Amino End Groups

In this example a monomer selected from one of the compounds (M1), (M2) and (M3) prepared as described above, or the monomer compound (M6), 2-(Trimethylammonio)ethylmethacrylate chloride (TMAEM.Cl⁻), was dissolved in methanol to form a solution containing 13 wt % of the monomer. Azobisisobutyronitrile (AIBN) was then added (0.6–12 wt % relative to the polymerisation mixture) to act as an initiator. Cysteamine hydrochloride (2–10 mol % relative to the amount of monomer) was used as a chain transfer agent. The solution was introduced into an ampule and bubbled through with nitrogen. The ampule was sealed and polymerisation was carried out at 50° C. for 24 hours. The polymer formed was precipitated into acetone or acetone-diethyl ether. In some cases, oligomers and low-molecular weight impurities were removed on a GPC column packed with SEPHADEX LH-50 in methanol, and polymer was separated from the methanol solution, again by precipitation into acetone-diethyl ether. Precipitated polymer was then filtered off, washed with acetone or diethyl ether and dried in vacuao Use of monomers (M1), (M2) or (M3) produced polymers terminating in a primary amino group at one end of the main chain and having side chains terminating in a (CH₂)ₙ—NH-BOC group. The BOC protection groups of the primary amino groups in the side chains of the cationic polymer were then removed as described under 8.2.1 above.

The molecular weight of the polycations can be varied by changing the amount of cysteamine, initiator or monomer concentration in the polymerization mixture.

Example 9
9.0 Synthesis of p(HPMA) Hydrophilic Polymers

To illustrate the preparation of hydrophilic polymers for use in conjunction with the above-described cationic polymers or other suitable cationic polymers to build shielded DNA complexes of the latter there is next described the preparation of some homopolymers with various reactive terminal groups based on free radical addition polymerisation of N-(2-hydroxypropyl)methacrylamide (HPMA) monomers.

9.1. Synthesis of poly[N-2-(hydroxypropyl) methacrylamide] with Carboxylic End Groups
9.1.1 Synthesis of poly[N-2-(hydroxypropyl) methacrylamide] with One Carboxylic End Group Poly[N-2-(hydroxypropyl)methacrylamide] (pHPMA) terminated in one carboxylic end group was prepared by radical solution polymerisation of HPMA in the presence of 3-mercaptopropionic acid as a transfer agent.

N-2-(hydroxypropyl)methacrylamide (4.2 g, 0.0293 mol) was dissolved in methanol (12 ml, 20 wt % of monomer). AIBN (0.1 g, 0.5 wt % of polymerisation mixture) and 3-mercaptopropionic acid (0.08 g, 2 mol % to monomer) was added. The solution was introduced into an ampule and bubbled through with nitrogen. The ampule was sealed and polymerisation was carried out at a temperature 60° C. for 24 hours. The polymer was precipitated by pouring the reaction mixture into an excess of a mixture of acetone-diethyl ether 3:1. The polymer was dissolved in methanol and purified on Sepharose LH60™ column (3.5×24cm). The polymer fraction was collected, methanol was evaporated and the polymer was precipitated into acetone.

9.1.2 Synthesis of poly[N-2-(hydroxypropyl)methacrylamide] with One or Two Carboxylic End Groups Polymerisation of HPMA was carried out in methanol, and the monomer concentration was 10 or 20% wt. 4,4'-azobis(4-cyanovaleric acid) was used as an initiator and its concentration was 0.1–2 wt % relative to the amount of polymerisation mixture. To facilitate the radiolabelling of the polymer N-methacryloyl tyrosinamide (prepared by the reaction of methacryloyl chloride with tyrosinamide in aqueous solution) was added (1 mol % relative to the monomer). The solution was introduced into an ampule and bubbled through with nitrogen. The ampule was sealed and polymerisation was performed at a temperature ranging from 50° C. to 60° C. for 24 hours. The polymer was precipitated into acetone and dried in vacuo. The carboxylic group content was estimated by titration.

9.2 Synthesis of poly[N-2-(hydroxypropyl)methacrylamide] with an End Amino Group Poly[N-2-(hydroxypropyl)methacrylamide] with an amino end group was prepared by free radical solution polymerisation of HPMA in the presence of cysteamine as a transfer agent.

N-2-(hydroxypropyl)methacrylamide (2.0 g, 0.014 mol) was dissolved in methanol (16.6 ml, 13.2 wtO/o of monomer), AIBN (0.014 g, 0.7 wt % of polymerisation. mixture) and cysteamine (0.2 g, 10 wt % to monomer) was added. The solution was introduced into an ampule and nitrogen was bubbled through. The ampule was sealed and polymerisation was carried out at 50° C. for 24 hours. Polymer was isolated by precipitation into 300 ml of acetone. The polymer was filtered off, dissolved in methanol and reprecipitated into diethyl ether.

The polymers prepared as described above were characterised as indicated below.

9.3 Characterisation of p(HPMA) polymers

The molecular weight distribution (weight average molecular weight $M_w$ and polydispersity $M_w/M_n$) of the hydrophilic poly(HPMA) polymers terminated in carboxylic or amino end groups was determined by fast-protein liquid chromatography (FPLC) on a column packed with Superose 12™ (Pharmacia) using 0.05M TRIS buffer pH=8.0 containing 0.5 M NaCl as a mobile phase.

The molecular weight distribution (weight average molecular weight $M_w$ and polydispersity $M_w/M_n$) of the cationic polymers was determined by FPLC on Sepharose 12™ using 0.25M sodium acetate buffer (pH=6.6) containing 0.5M NaCl and 0.028M tetramethylammonium chloride.

Example 10

Synthesis of p(HPMA) Graft Block Copolymers

As described in Example 7, after self-assembly with DNA the cationic polymers may be linked to one or more hydrophilic polymers to form in effect graft block copolymers, this being achieved by providing reactive groups spaced along the length of the cationic polymers. In some embodiments, the preferred reactive groups for bringing about this coupling, either at the ends or on side chains along the main polymer backbone, are conveniently provided by reactive amine or thiol groups. The present example, shown in the diagram of FIG. 3 of the accompanying drawings, describes the preparation of graft copolymers by the reaction of poly(HPMA)-COOH with cationic polymers bearing primary amino groups in their side chains [poly(Lys), poly(Ma-Gly-NH—(CH$_2$)—NH$_2$, poly(Ma-NH—(CH$_2$)—NH$_2$, etc.].

In practice, this reaction would be carried out after self-assembly of the cationic polymer with nucleic acid to form the initial cationic polymer nucleic acid polyelectrolyte complex, but for the sake of simplicity a typical procedure followed for the synthesis of such graft block copolymers which may be represented as polycation-gr-poly(HPMA) is described omitting the first step of assembling the nucleic acid complex. In this typical procedure:

Poly(HPMA)-COOH was dissolved in water (10 wt %) and water-soluble carbodiimide EDC (N-(3-dimethylaminopropyl)-N'-ethylcarbodiimide hydrochloride) was added in excess (5×). Polycationic polymer [poly(Lys), poly(Ma-Gly-NH—(CH$_2$)—NH$_2$), etc.] was dissolved in water and neutralized by dilute HCl to pH 5. Both polymer solutions were mixed and stirred for 10 hours. The ratio of polymers (polycation: poly(HPMA) was 1:0.05–1:0.25. The graft copolymer was purified by dialysis in water and isolated by freeze drying.

The reaction of polycations with poly(HPMA)-COOSu can be carried out similarly, i.e. in water, pH 5. This reaction does not require the presence of EDC in the reaction mixture.

Example 11

Self-assembly with DNA of Cationic Polymers Bearing Groups Which Become Protonated in the Endosomal pH Range, and Subsequent Coating With Reactive Hydrophilic Polymers Which are Biodegradable in the Polymer Backbone.

Complexes can self-assemble between DNA and cationic polymers which are pH-responsive over the endosomal range, such as poly(ethylene imine). These are attractive polymers for DNA complexation since they possess good ability to transfect cells, perhaps by the mechanism described as the "Proton Sponge hypothesis" (Behr, Chimica 51, 34, 1997). However it is hard to define precisely their degree of ionisation at neutral pH, and therefore they should be used at weight ratios determined experimentally to mediate efficient complex formation. In this example, such a pH-responsive polymer was prepared by partial substitution of poly(L-lysine) with L-histidine. It is important that such polymers retain a significant component of reactive (primary or secondary) amino groups if surface modification is to be achieved using polymers bearing reactive esters. In this example the histidinylated poly(lysine) was allowed to self-assemble with DNA and the resulting particles were stabilised by surface modification using a hydrophilic polymer bearing pendant reactive esters. The hydrophilic polymer used was formed from alternating blocks of poly(ethylene glycol) and tripeptides, designed to introduce proteolytic degradability into the polymer backbone.

11.1 Preparation of Diamine Linker NH$_2$-GluLysGlu-NH$_2$ (a) $1^{st}$ Stage—Synthesis of N,N'-Bis(tert-butoxycarbonyl)lysine:

A solution of Boc2O (25 g, 114 mmol) in dioxane (50 ml) was added to a solution of lysine monohydrochloride (10 g, 54 mmol) and NaOH (4.4 g, 108 mmol) in water (50 ml). The reaction mixture was stirred at 45° C. until it (became clear (about 2.5 h). The solvent was evaporated to a final volume of about 20 ml and the resulting solution was diluted with 100 ml of water and washed with petrolether (50 ml). The aqueous layer was acidified with aqueous KHSO$_4$ (8 g in 50 ml) to pH 3 and the product was extracted with ethyl acetate (3×50 ml). The collected extracts were washed with aqueous NaCl and dried over $Na_2SO_4$. Ethyl acetate was taken off under reduced pressure and 18.5 g (53 mmol) of the colourless oily product was obtained.

(b) $2^{nd}$ Stage—Synthesis of N,N'-Bis(tert-butoxycarbonyl) lysine Benzyl Ester:

N,N-Bis(tert-butoxycarbonyl)lysine (18.5 g, 53 mmol), benzyl alcohol (5.5 ml, 53 mmol), 4-(dimethylamino) pyridine (DMAP) (1.2 g, 10 mmol) and DCC (12 g, 58 mmol), were dissolved in ethyl acetate (100 ml) at 0° C. The reaction mixture was stirred for 20 min at 0° C. and then left for 5 h at 20° C. The progress of the reaction was checked by TLC (silica gel/ethyl acetate). The precipitate was filtered off and the filtrate was washed with aqueous $CuSO_4$ solution (3×50 ml). The organic layer was evaporated to dryness and an oily product was used for the next reaction.

(c) $3^{rd}$ Stage—Synthesis of Lysine Benzyl Ester Bis (trifluoroacetate):

N,N'-Bis(tert-butoxycarbonyl)lysine Benzyl Ester (about 50 mmol) was dissolved in TFA (20 ml, 260 mmol). The reaction mixture was kept 1 h at 20° C. in a flask equipped with $CaCl_2$ tube. TFA was removed under reduced pressure, the residue was dissolved in water (100 ml) and washed with diethyl ether (2×50 ml) to remove the unreacted benzyl alcohol. The water layer was filtered and freeze dried. An amorphous hygroscopic product was used in the next reaction.

(d) 4th Stage—Synthesis of N,N'-Bis(tert-butoxycarbonyl-benzylglutamyl)lysine Benzyl Ester:

To an ice-cooled solution of acid (8 g, 21 mmol), Lysine Benzyl Ester Bis(trifluoroacetate): N,N'-Bis(tert-butoxycarbonyl)lysine Benzyl Ester 4.87 g (10.5 mmol), triethylamine (2.93 ml, 21 mmol) and HOBt (2.84 g, 21 mmol) in THF (100 ml, freshly distilled) a solution of DCC (4.77 g, 23 mmol) in THF (30 ml) was added. The reaction was carried out for 1 h at 0° C. and for 5 h at 20° C. with stirring. The precipitate was removed by filtration, THF was evaporated to dryness and the viscous residue was dissolved in ethyl acetate (200 ml). The solution was successively washed with aqueous 5% $NaHCO_3$ (50 ml), 5% citric acid (100 ml) and aqueous 5% $NaHCO_3$ (50 ml). The organic layer was dried over $Na_2SO_4$, filtered and evaporated to dryness. The residue was dissolved in diethyl ether and evaporated again. The amorphous solid-was recrystallized from ether/hexane (3:1). The yield, melting at 89–920C was 6.0 g (6.86 mmol, 65%).

(e) $5^{th}$ Stage—Synthesis of N,N'-Bis(-benzylglutamyl) lysine Benzyl Ester Bis(trifluoroacetate):

N,N'-Bis(tert-butoxycarbonyl-benzylglutamyl)lysine Benzyl Ester (0.5 g, 0.57 mmol) was dissolved in TFA (3 ml, 0.39 mmol) and the mixture was left for 1 h at 20° C. TFA was removed in vacuo and the residue was covered with dry diethyl ether. After 24 h., the non-crystalline solid was dissolved in 10 ml water. The aqueous layer was separated and the traces of ether were removed under reduced pressure. The water solution was freeze-dried yielding 0.6 g (98%) of a hygroscopic product 11.2 Preparation of Multiblock Copolymer, poly(pEG-GluLysGlu) (pEG-Block Copolymer Containing-ONp Groups)

(a) $1^{st}$ Stage—Synthesis of pEG-bis(succinimidyl carbonate) (pEG-BSC):

pEG 2000 (3.6 g, 1.8 mmol) dried by azeotropic removal of toluene was dissolved in pyridine (20 ml) together with 4-(N,N-dimethyl-amino)pyridine (88 mg, 0.72 mmol) and mixed with a solution of disuccinimidyl carbonate (1.8 g, 7.2 mmol) in acetonitrile (15 ml). The reaction mixtLre was left in a darkness at 25° C. over weekend. The solvents were removed by rotavapor, the residue was dissolved in warm ethyl acetate (50 ml, dried and distilled) and the product was isolated by precipitation and filtration after addition of diethyl ether (50 ml) to the cooled ethyl acetate solution. This operation was repeated three times yielding 3.1 g of the active carbonate.

(b) $2^{nd}$ Stage—Synthesis of poly[pEG-GluLysGlu(OBz)] By Interfacial Polymerization and Hydrogenation:

The solution of pEG-BSC (1.3 g, 0.572 mmol) in methylene chloride (20 ml) was added to the mixture of N,N'-Bis(-benzylglutamyl)lysine Benzyl Ester Bis (trifluoroacetate) (0.516 g, 0.572 mmol) and sodium bicarbonate (230 mg, 2.73 mmol) in water (20 ml) under vigorous stirring at 25° C. The reaction mixture was acidified with 0.1 M HCl to pH 3 after 5 hrs of stirring. The organic layer was separated, washed with aq. NaCl and dried over anhydr. $Na_2SO_4$. The drying agent was filtered off and the filtrate was concentrated to the volume approx. 10 ml. The precipitation of the polymer to diethyl ether failed (results in an oily layer). The solvent was removed under vacuum, the residue was suspended in water (white emulsion) and freeze-dried. Yield 1.1 g of polymer.

The molecular weight (weight average) of the polymer obtained depends very much on reaction conditions (stirring speed, mutual ratio of reactants, etc.). Usually $M_w$ will be in the range 15000–30000 Da's.

The polymeric benzyl ester (800 mg) produced was then dissolved in ethanol (10 ml) with a drop of acetic acid and hydrogenated on paladium catalyst (Pd/C, 10%) 3 hrs. The reaction mixture was bubbled with nitrogen, the catalyst was filtered off and ethanol was removed under vacuum. The residue was dissolved in water and freeze-dried yielding over 700 mg of hygroscopic polymer.

Figure 4:
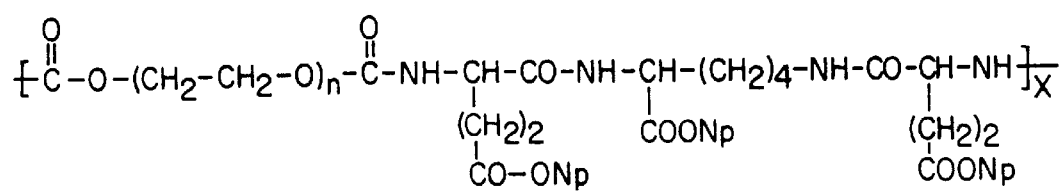
FIG. 4 is a diagram illustrating the structure of the alternating poly(ethyleneglycol)-oligopeptide block copolymer.

(c) $3^{rd}$ Stage—Synthesis of poly[pEG-GluLysGlu(ONp)]:

The polymeric acid (200 mg), 4-nitrophenol (100 mg) and N,N'-dicyclohexyl carbodiimide (140 mg) were dissolved in methylene chloride (2 ml) at 0° C. A gel was formed almost immediately (probably acid anhydride formation among the COOH groups) but dissolved during next 5 minutes. The reaction mixture was kept at 4° C. for 72 h. A drop of acetic acid was added and the precipitated urea derivative was filtered off 20 minutes later. Precipitation of the polymer to diethyl ether was unsuccessful (oil was formed). The solvents were evaporated and the polymer was purified (removal of 4-nitrophenol) by GPC (SEPHADEX LH20, methylene chloride). The polymer was isolated by freeze-drying from benzene resulting in a hydroscopic yellowish powder which however melts when not kept under vacuum. Yield 200 mg. The molecular weight of the pEG blocks was about 2000 and the structure of this product is illustrated in FIG. 4 of the drawings.

11.3 Synthesis of pLL Partially Substituted With Histidine (pLL-His)

Poly-L-lysine (pLL) (100 mg) was dissolved in 60 ml phosphate buffer, pH 7.0, containing 0.1 M sodium chloride. N-hydroxysuccinimide ester of histidine (Boc-His(Boc)-OSu) (110 mg) was dissolved in 10 ml dimethylsulfoxide and added to the solution of pLL. After 2 hrs reaction at room temperature, the solution was dialysed against 0.01 N hydrochloric acid and the product was isolated by lyophilization. The product obtained was dissolved in 10 ml trifluoroacetic acid and the solution stirred for 2 hrs at room temperature. Trifluoroacetic acid was evaporated under vacuum, the product was dissolved in water and dialysed against 0.01 N hydrochloric acid and then against water.

Figure 5:
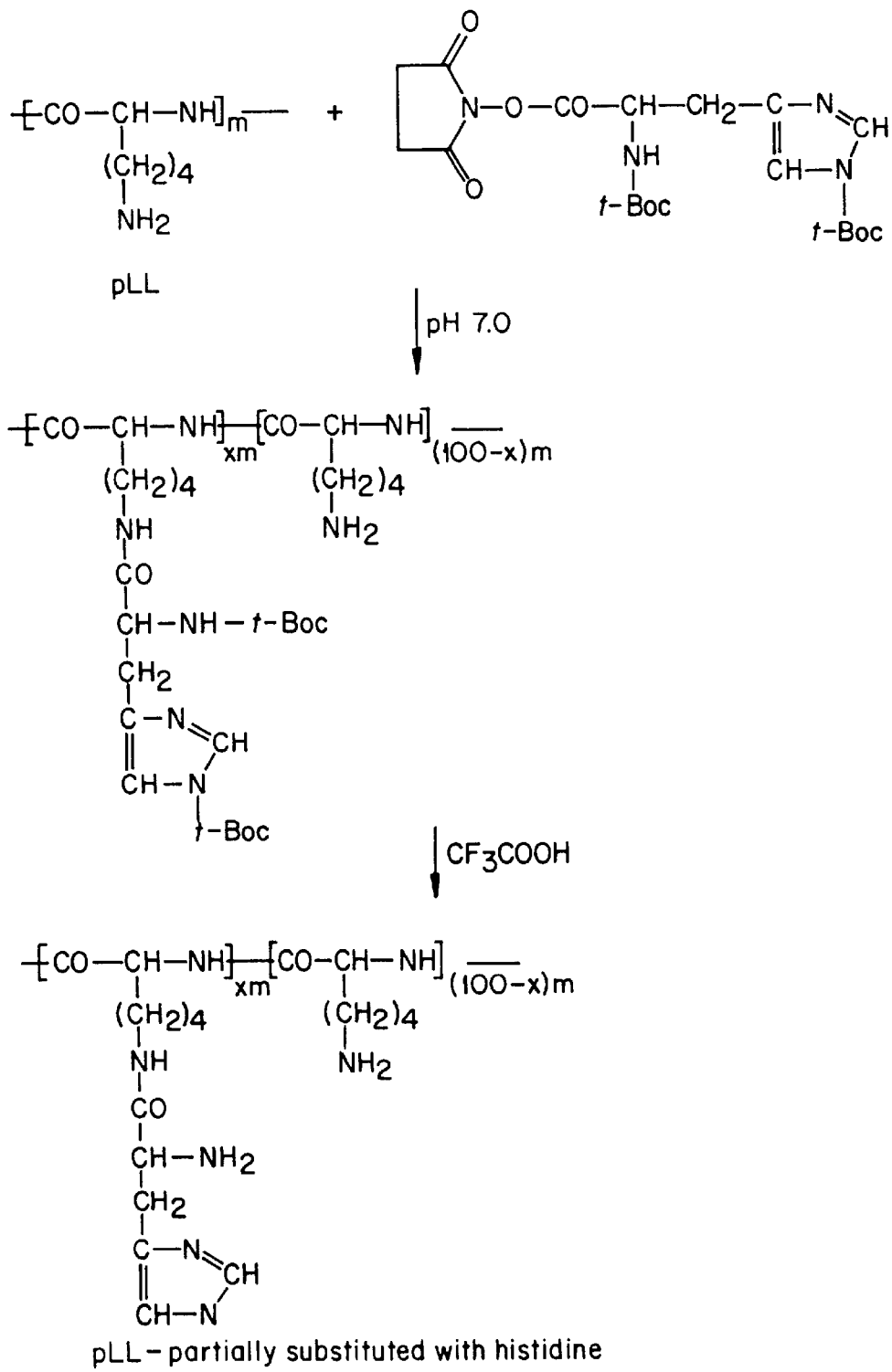
FIG. 5 is a diagram of the synthesis of pLL—partially substituted with histidine.

The degree of substitution, determined by $^1$H NMR, was 30%, and the overall reactions are illustrated in FIG. 5 of the drawings.

Any desired degree of substitution (5–30%) could be obtained by varying the molar ratio between pLL and Boc-His(Boc)-OSu.

11.4 Self Assembly of Complexes Between DNA and Partially Histidine-Substituted poly(L-lysine), and Subsequent Stabilisation by Surface Modification Using pEG-peptide-ONp Repeating Polymer.

In this experiment to demonstrate complex formation and stabilisation, DNA (20 μg/ml) was incubated, at room temperature in water, with ethidium bromide (400 ng/ml) and the fluorescence ($\lambda_{ex}$ 366, $\lambda_{em}$ 590) was set to 100%. Small volumes of pLL-His were then added and the fluorescence was read. The signal observed was plotted and displayed a sigmoidal fall with increasing amount of pLL-His added. The steepest tangent to the curve was extended to the x-axis, and the amount of pLL-His corresponding to the intercept (charge ratio 0.9) was used as the minimum quantity capable of efficient complex formation. Fresh complexes were then formed using 50 μg/ml pLL-His and 40 μg/ml DNA, and allowed to stand for 1 h.

Reactive pEG-peptide-ONp repeating polymer (dissolved in DMSO) was added to the preformed complexes in borate solution (pH 7.4) to a final concentration of 200 μg/ml. The solution went gradually yellow as free paranitrophenol was released. The stability of the complexes to albumin was determined, by adding ethidium bromide (400 ng/ml) either before or after the polyelectrolyte condensation, with subsequent addition of albumin and measurement of fluorescence as above. Irrespective of the time of addition of ethidium bromide, the presence of the reactive pEG-peptide repeat polymer was found to make the complexes completely resistant to disruption by albumin even at physiological serum concentrations.

Figure 6A:
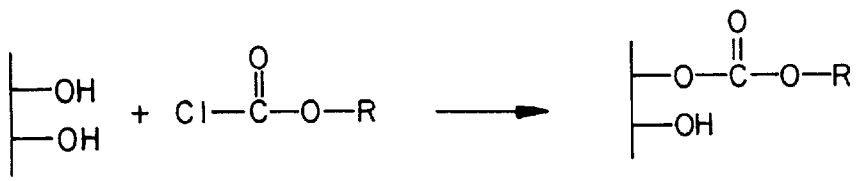
FIG. 6A is a diagram of the synthesis of pHEG-ONp.
Figure 6B:
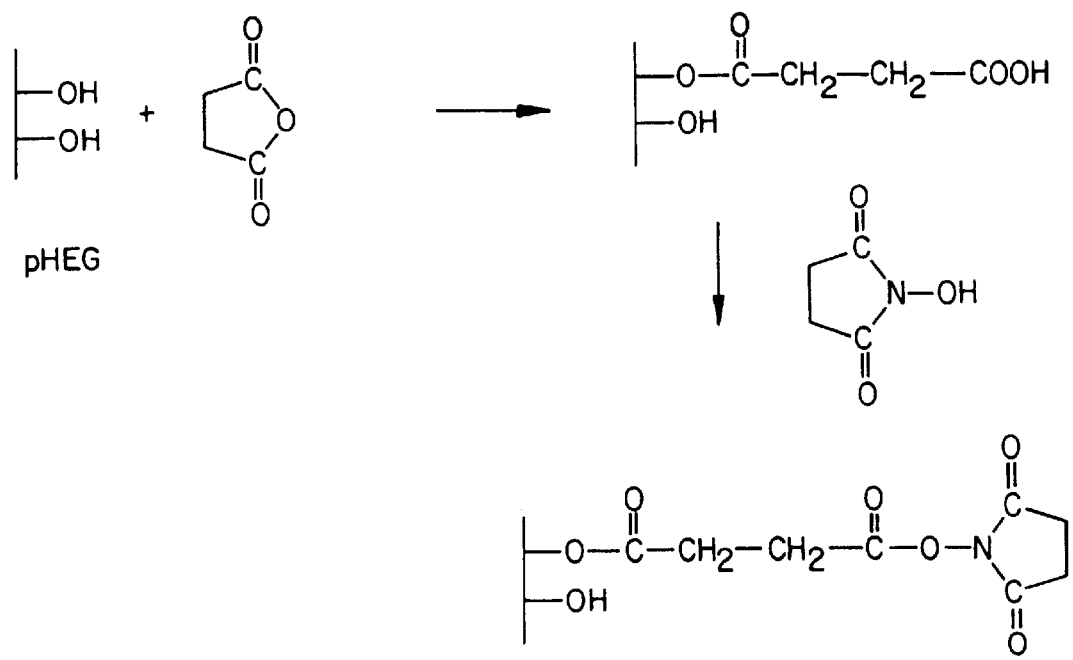
FIG. 6B is a diagram of the synthesis of the synthesis of pHEG-succinate and subsequent conversion to its N-hydroxysuccinimide ester.

Example 12
Synthesis of Reactive Polymers Based on poly[N-(2-hydroxyethyl)-L glutamine] (pHEG)

pHEG is a promising material to act as the main chain of the hydrophilic polymer for surface modification of preformed cationic polymer/DNA complexes, since it is known to be readily biodegradable, facilitating activation of the DNA under appropriate conditions. It is also multifunctional and can incorporate several reactive groups, even of more than one type. In this example some synthetic routes undertaken to demonstrate the versatility of this polymer in this application are described and illustrated in FIGS. 6A and 6B of the drawings.

12.1 Synthesis of pHEG-ONp:

0.2 g of pHEG (1.16 mmol units) and 12.8 mg of 4-dimethylaminopyridine (0.105 mmol) were dissolved in 10 ml of N-methyl-pyrrolidinone/pyridine (vol. ratio 4/1) and cooled to 0° C. 140.6 mg 4-nitrophenyl chloroformate (0.7 mmol) was added and the mixture was stirred for 4 h at 0° C. The activated polymer was precipitated in anhydrous ethanol/ether (vol. ratio ½). The polymer was collected and dried.

The degree of substitution was determined by dissolving the activated pHEG in 0.1 M sodium hydroxide and measuring the absorbance in a UV-spectrometer ($\lambda_M$=402 nm; $\epsilon_M$=18400 L.mol$^{-1}$.cm$^{-1}$). The degree of substitution was 8.7 mole %.

12.2 Synthesis of pHEG-succinate and Subsequent Conversion to its N-Hydroxysuccinimide Ester (a) 1$^{st}$ Stage—Synthesis of pHEG-succinate:

0.25 g of pHEG (1.45 mmol units) and 56 mg of succinic anhydride (0.56 mmol) were dissolved in 4 ml of dimethylformamide. Then, a solution of 14 mg of 4-dimethylaminopyridine (0.12 mmnol) in 1 ml dimethylformamide was added. The reaction mixture was stirred for 24 h at 40° C. The reaction product was isolated by precipitation in anhydrous ethanol/ether (vol. ratio ½). The dried precipitate was subsequently dissolved in water and purified by preparative gel filtration (SEPHADEX G-25, eluent: water, flow: 2 ml/min). The polymer was collected by freeze-drying.

The degree of esterification was determined either by titriretric analysis of the carboxylic acid content or by $^1$H-NMR analysis and was 10.1%.

(b) 2$^{nd}$ Stage—Activation of pHEG-succinate with N-hydroxy-succinimide:

0.25 g of pHEG-succinate (1.45 mmol units, 10 mole % succinate substitution) was dissolved in 10 ml dimethylformamide. The solution was cooled to 0° C. and 34 mg of N-hydroxysuccinimide (0.29 mmol) and 0.1 16 mg of N,N-dicyclohexylcarbodiimide (0.29 mmol) were added under stirring.

After the mixture was stirred overnight at room temperature, precipitated dicyclohexylurea was removed by filtration. The polymer was precipitated in anhydrous ethanol/ether (vol. ratio ½). The polymer was collected by filtration and dried.

The degree of esterification was calculated on the basis of N-hydroxysuccinimide absorption after alkaline hydrolysis ($\lambda_M$=260 nm; $\epsilon_M$=8000 L.mol$^{-1}$.cm$^{-1}$) and was 9.5%.

Figure 7A:
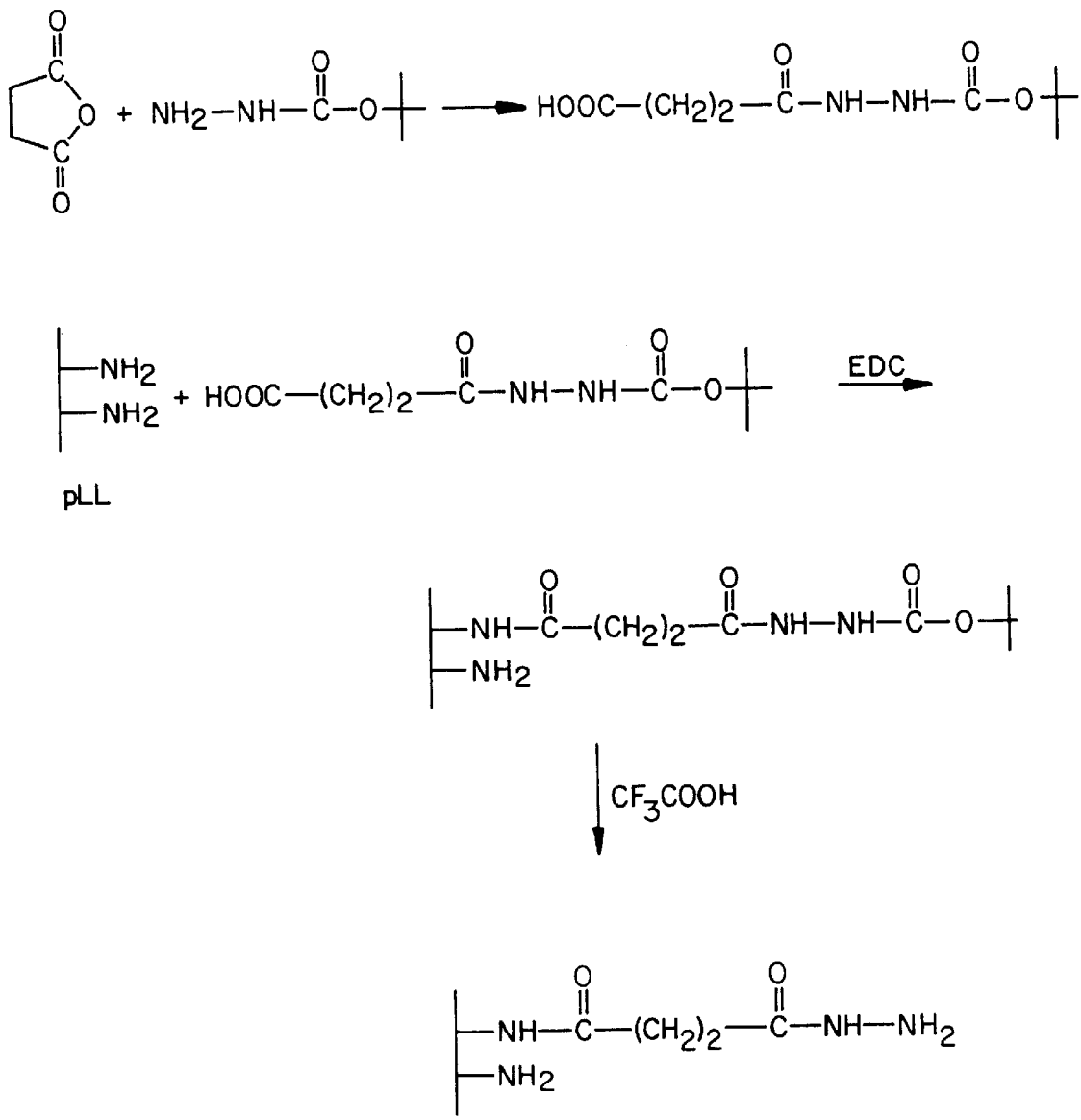

Example 13
Modification of poly(L-lysine) (pLL) with Hydrazide, and Subsequent Surface Modification of Complexes Formed with DNA Using Polymers Bearing Multiple Reactive Aldehyde Groups Attachment of surface coating polymers though bonds which are acid unstable and labile at endosomal pH is one important aspect of this invention. There are several chemical strategies suitable for this purpose, but one is exemplified here. Reactions involved are illustrated diagrammatically in FIGS. 7A and 7B of the drawings.

13.1 Synthesis of Hydrazide-Modified pLL (a) 1$^{st}$ Stage—Coupling of Polylysine with Succinic Acid t-butyl-oxycarbonylhydrazide.

0.2 g polylysine (1.56 mmol units) and 20.64 mg succinic acid t-butyloxycarbonylhydrazide (0.156 mmol) were dissolved in water and the pH of the solution was adjusted to 5.0 with HCl.

Subsequently, 300 mg of 1-ethyl-3-(3-dimethylaminopropyl)-carbodiimide (EDC) (1.56 mmol) in water were added to this solution. The pH was maintained at 5.0 with HCl during the reaction. After stirring overnight, the solution was dialyzed for 48 h against water. The polymer was collected by freeze-drying.

The degree of substitution was determined by means of $^1$H-NMR-spectroscopy and was 7%.

(b) 2$^{nd}$ Stage—Removal of the t-butyloxycarbonyl Protecting Group 0.2 g of this modified polylysine derivative (above) was dissolved in 10 ml trifluoroacetic acid. The mixture was stirred for 1 h and the solvent was evaporated. The residue was dissolved in water and further dialyzed for 48 h. The polymer was collected by freeze-drying.

The degree of substitution was determined by means of $^1$H-NMR-spectroscopy and was 6.8%.

13.2 Synthesis of pHEG-aldehyde

Poly(γ-benzyl-L-glutamate) (PBG, 100 mg) was dissolved in 1.6 ml dry dimethylformamide. 2-Hydroxypyridine (217 mg) was added to the solution of PBG. Aminoethanol (0,22 ml) and 3-amino-1,2-propanediol (0,07 ml) were added dropwise to the above solution. After complete aminolysis (the reaction is followed by IR-spectroscopy) the polymer was isolated by precipitation in cold ether. The product was filtered, dried and isolated by preparative size exclusion chromatography on a SEPHADEX G-25 column followed by lyophilization.

The pHEG-aldehyde is prepared by oxidation of the yicinal diol groups in the polymer prepared in the above step. The polymer (100 mg) was dissolved in 20 ml water and protected from the light. $NaIO_4$ (53 mg) was added and the reaction was allowed to continue for 4 hrs in dark. The polymer was isolated by size exclusion chromatography on a SEPHADEX G-25 column and lyophilized.

The content of aldehyde groups, determined by $^1$H NMR, was 20%.

The composition of the polymer and the content of the aldehyde groups could be varied by changing the molar ratio between the components.

13.3 Formation of a Complex of DNA with the Partially Hydrazide-Modified Polylysine Followed by Grafting with the pHEG-aldehyde.

The partially hydrazide-modified polylysine derivative was mixed in water with Calf Thymus DNA (Sigma) at charge ratio 2.0 giving a polycation/DNA polyelectrolyte complex. The mixture was added to a solution of pHEG-aldehyde in citric acid pH=5.0 (0.1 M) and stirred for 2 h.

The amount of pHEG-aldehyde grafted onto the polyelectrolyte complex was estimated by amino acid analysis of glutamic acid following acid hydrolysis of pHEG in 6N HCl.

Figure 8:
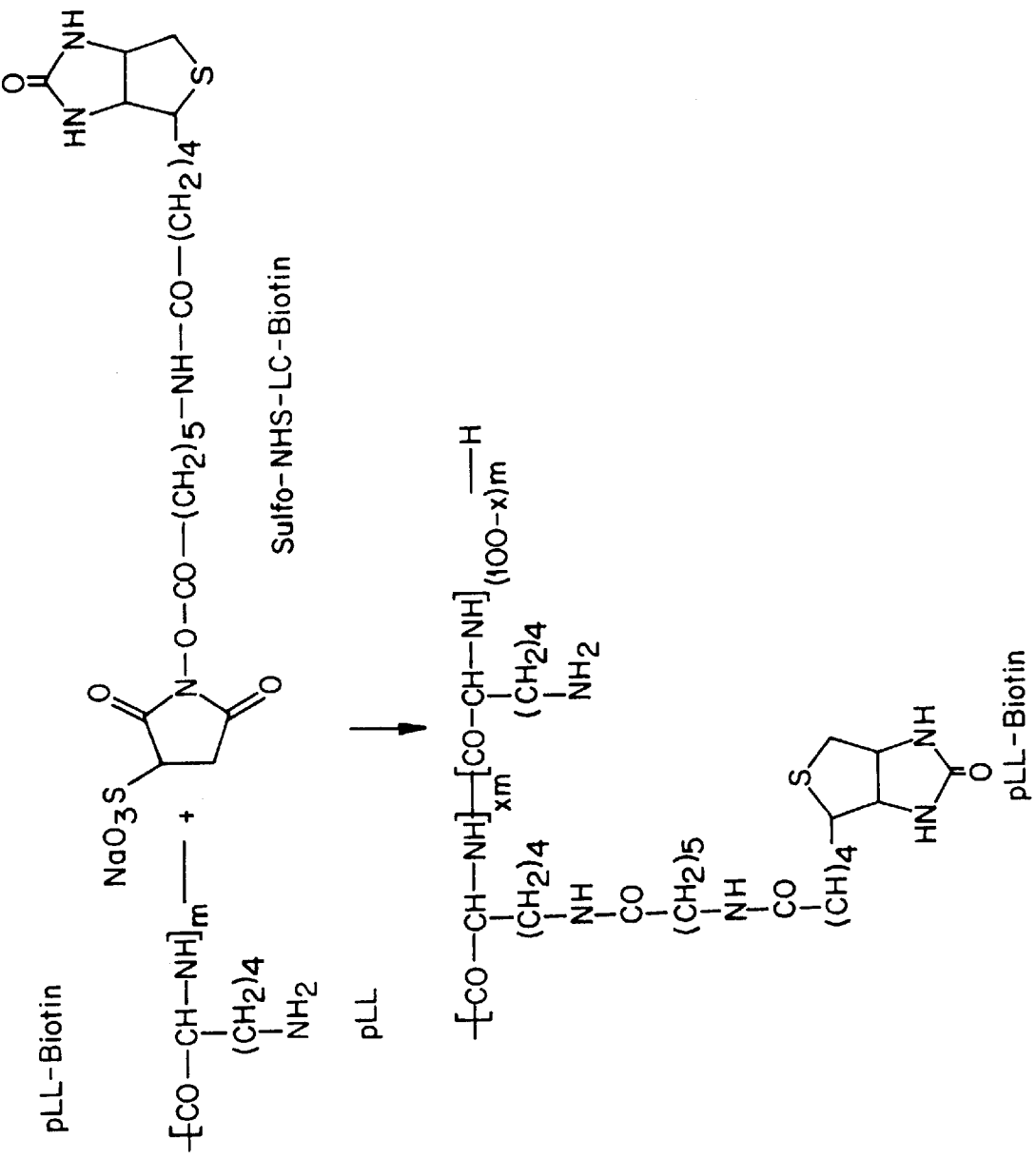
FIG. 8 is a diagram of the synthesis of pLL-biotin.

Example 14
Preparation of poly(L-lysine) (pLL) Molecules with Substituent Groups Suitable for Varied Chemistry of Attachment of Stabilising Polymers and Other Agents to Preformed Modified pLL/DNA Complexes This is exemplified by the synthesis of pLL-biotin according to the reaction scheme illustrated in FIG. 8 of the drawings.

Poly-L-lysine (pLL) (100 mg) was dissolved in 15 ml phosphate buffer pH 7,0 containing 0.1 M sodium chloride. Sulfo-N-hydroxysuccinimide ester of Biotin (Sulfo-NHS-LC-Biotin) (22 mg) was dissolved in 3 ml water and added to the solution of pLL. After 4 hrs stirring at room temperature the solution was dialysed against 0.01 N hydrochloric acid and then against water. The product was isolated by lyophilization.

The product could be isolated also by a preparative size exclusion chromatography on a SEPHADEX G-25 column followed by lyophilization.

The degree of substitution, determined by $^1$ H NMR, was 5%.

The degree of substitution could be varied by changing the molar ratio between pLL and Sulfo-NHS-LC-Biotin.

Example 15
Synthesis of poly-[N-(2-hydroxyethyl)-L-glutamine] (pHEG) Polymers Bearing Both Reactive paranitrophenyl (ONp) Esters and also poly(ethylene glycol) (pEG) Side Chains Reactive hydrophilic polymers such as the pEG-pHEG-ONp material described here can be used for the stabilisation of complexes formed between cationic polymers and DNA. In addition to lateral stabilisation against disruption by protein binding, they have the added benefit of introducing a layer of flexible, hydrophilic polymer onto the surface of the particle which should further decrease non-specific and unwanted interactions with the biological environment
(a) Stage 1—Synthesis of 4-nitro-phenyl-chloroformate Activated pHEG.

0.5 g ($2.91 \times 10^{-3}$ mol) of poly-[N-(2-hydroxyethyl)-L-glutamine] (PHEG) was dissolved in 20 ml anhydrous N-methyl-pyrollidon(NMP)/Pyridine(Pyr) mixture (4/1, vol/vol) and stirred at 0° C.

0.41 g ($2.03 \times 10^{-3}$ mol) 4-nitro-phenyl-chloroformate and 0.037 g ($3.04 \times 10^{-4}$ mol) 4-dimethyl-amino-pyridine (DMAP) were added. The reaction mixture was stirred for 4 hours at 0° C.

The activated pHEG was precipitated in anhydrous 2-propanol, filtered, washed with 2-propanol and ether and finally dried.

The degree of activation was determined with UV-spectroscopy:

2 mg of the activated pHEG was dissolved in 10 ml of 0.1 N NaOH. The concentration of the liberated sodium 4-nitrophenolate was determined with UV-spectroscopy ($\lambda$=402 nm).

The degree of activation is expressed as the amount of activated units per 100 repeating units in the polymer: 7 mol %

(b) Stage 2—Synthesis of pHEG-pEG.

4-nitrophenyl-chloroformate activated pHEG (0.5 g, $2.03 \times 10^{-4}$ mol reactive ester groups) was dissolved in 10 ml of anhydrous dimethylsulfoxide (DMSO)/Pyr mixture (4/1, vol/vol).

pEG-NH2 (Mw 5000) (1.02 g, $2.03 \times 10^{-4}$ mol) was added to the activated pHEG.

The reaction mixture was stirred for 48 hours at room temperature. The product was then precipitated in excess ether/ethanol (10/1,v/v), filtered and dried.

Unreacted pEG-$NH_2$ was removed by ion exchange chromatography. (IRC-50 resin, eluent=water). The collected pHEG-pEG fraction was recovered by freeze drying.

The degree of substitution was determined by $^1$ H NMR-spectroscopy.

The degree of substitution was expressed as the amount of substituted units per 100 repeating units in pHEG: 3 mol % (=46 weight %)

(c) Stage 3—Synthesis of 4-nitro-phenyl-chloroformate Activated pHEG-pEG.

0.1 g pHEG-$pEG_{5000}$ (3%) (54 weight % pHEG =0.054 g pHEG=$3.14 \times 104$) was dissolved in 20 ml anhydrous NMP/Pyr mixture (4/1,v/v). The solution was stirred at 0° C.

44 mg ($2.2 \times 10^{-4}$ mol) 4-nitrophenyl-chloroformate and 4 mg ($3.3 \times 10^{-5}$ mol) DMAP were added. The reaction mixture was stirred for 4 hours at 0° C.

The activated pHEG-pEG precipitated in anhydrous 2-propanol, filtered and dried.

The degree of activation was determined by UV-spectroscopy as described above: 5 mol %

The degree of activation was expressed as the amount of activated units per 100 repeating units in the pHEG backbone.

Reactions involved are illustrated in FIG. 9 of the drawings.

Example 16
16.0 Incorporation of Membrane Disrupting Agents

Using biologically inert synthetic polymers based on polymerisation of unsaturated monomers such as methacrylamide or similar acrylic based monomers, the complexes will generally have a compact and roughly spherical core composed of condensed DNA and the cationic polymer material with a plurality of the hydrophilic polymer molecules around the core to form a coating and steric shield. Polyelectrolyte complexes produced using such synthetic polymers formed by addition polymerisation of acrylic based monomers, however, may sometimes be relatively inactive in regard to disruption of cellular membranes, unlike complexes having an extended configuration formed by using poly(L)lysine cationic polymers, and for this reason it may often be preferred to incorporate additional membrane disrupting or permeabilising fusogenic agents, e.g. oleyl lipid groups or fuisogenic peptides, which may be released within the interior of a target cell following endocytosis. These additional compounds, as with specific targeting groups previously referred to, and the hydrophilic polymer blocks, will often be coupled to components of the complex via pH-labile or enzymatically biodegradable linkages, as has also been previously mentioned. Specific examples are described below.

16.1 Synthesis of Partially Oleylated pTMAEM.Cl

In one procedure forming the subject of the present example, membrane disruptive oleyl blocks are coupled as esters, with glycerol for example. via a hydrolytic unstable or biodegradable linkage direct to a cationic polymer block that in the assembly of the polyelectrolyte complex forms part of the core portion containing the nucleic acid.

In this specific example a block copolymer for introducing an oleyl lipid group into a DNA complex carrier vehicle of the invention was prepared using pTMAEM.Cl having a terminal $NH_2$ group, this being made by radical polymerization in the presence of cysteamine which acts as a chain transfer agent (see Example 8.2.2). 0.32 g of the pTMAEM.Cl—$NH_2$ (Mw 10,000) was suspended in 1.5 ml DMSO and 12.2 mg oleyl succinimide ester was added together with 5 mg triethylamine. The reaction mixture was stirred for 24 hours at room temperature, and the polymer was purified by precipitation into acetone and isolated by filtration. Final purification was carried out on GPC in methanol (SEPHADEX LH-60). Other amino terminated cationic polymers that will complex with DNA could of course also be used.

16.2 Synthesis of Partially Oleylated pLL

In this example poly(L)lysine (pLL) (100 mg) was dissolved in 60 ml phosphate buffer pH 7.0 containing 0.1 M sodium chloride. Oleyl chloride (25 µl) dissolved in 3 ml dimethylsulfoxide was then added to the solution of pLL. Triethylamine (13 µl) was added to the solution and the mixture was stirred for 24 hours. The solution was dialysed against 0.01 N hydrochloric acid and then against water. The product was isolated by lyophilization.

The degree of substitution, determined by $^1$H NMR, was 7%.

16.3 Synthesis of a Partially Modified pLL Incorporating Fusogenic Peptide Linked via a Sulphide Bond In this Example, poly(L)lysine is partially modified with m-maleimidobenzoyl-N-hydroxysuccinimide ester (MBS) and the reaction product is then reacted with a fusogenic peptide having a reactive thiol group so that this peptide is grafted on to the main polymer chain.

A typical experimental procedure is as follows:

Poly(L)lysine (100 mg, MW=20000) is dissolved in 50 ml phosphate buffer pH 7.0 containing 0.1 M sodium chloride. m-Maleimido benzoyl-N-hydroxysuccinimide ester (MBS) (15 mg) is dissolved in 2 ml dimethylsulfoxide and added to the solution of pLL. After stirring at room temperature for 2 hours the solution is purified by dialysis against 0.01 N hydrochloric acid and then against water. The product (pLL-MBS) is isolated by lyophilization. The degree of substitution determined by $^1$H NMR, is 5%.

The pLL-MBS (50 mg) is then dissolved in 15 ml phosphate buffer pH 7.0 (oxygen-free). The fusogenic peptide having the reactive —SH group dissolved in phosphate buffer (15 ml) pH 7 (oxygen-free), and containing 2 ml EDTA, is then added to the solution of pLL-MBS. The system is kept under argon atmosphere and stirred during 2 hours at room temperature. The solution is purified by dialysis against 0.01 N hydrochloric acid and then against water. The product is isolated by lyophilization. This reaction scheme is illustrated in FIG. 10 of the drawings.

16.4 Synthesis of a Partially Modified pLL Incorporating Fusogenic Peptide Linked via z Disulphide Bond In this variation poly(L)lysine is partially modified with N-succinimidyl 3-(2-pyridyldithio) propionate (SPDP) and the reaction product is then reacted with a fusogenic peptide having a reactive thiol group.

Again a typical experimental procedure is as follows:

Poly(L)lysine (100 mg, MW=20000) is dissolved in 30 ml phosphate buffer pH 7 containing 0.1 M sodium chloride. SPDP (15 mg) is dissolved in 3 ml ethyl alcohol and added to the solution of pLL. After 2 hours reaction at room temperature the product is dialysed against 0.01 N hydrochloric acid and then purified by preparative size exclusion chromatography using SEPHADEX G-25. The product is isolated by lyophilization.

The degree of substitution (5 mol %) is determined by UV spectroscopy ($\lambda$=343 nm) after the reaction of the polymer with dithiotreitol (DTT).

The poly(L)lysine—SPDP (100 mg) is next dissolved in oxygen-free phosphate buffer (25 ml) at pH 7.4. A solution of fusogenic peptide in the same buffer (oxygen-free) then is added and the solution is stirred at room temperature for 4 hours under argon. After dialysis against 0.01 N hydrochloric acid the product is further purified by preparative size exclusion chromatography using SEPHADEX G-25 and lyophilized.

The degree of grafting obtained of the fusogenic peptide may be of the order of 5%.

Figure 11:
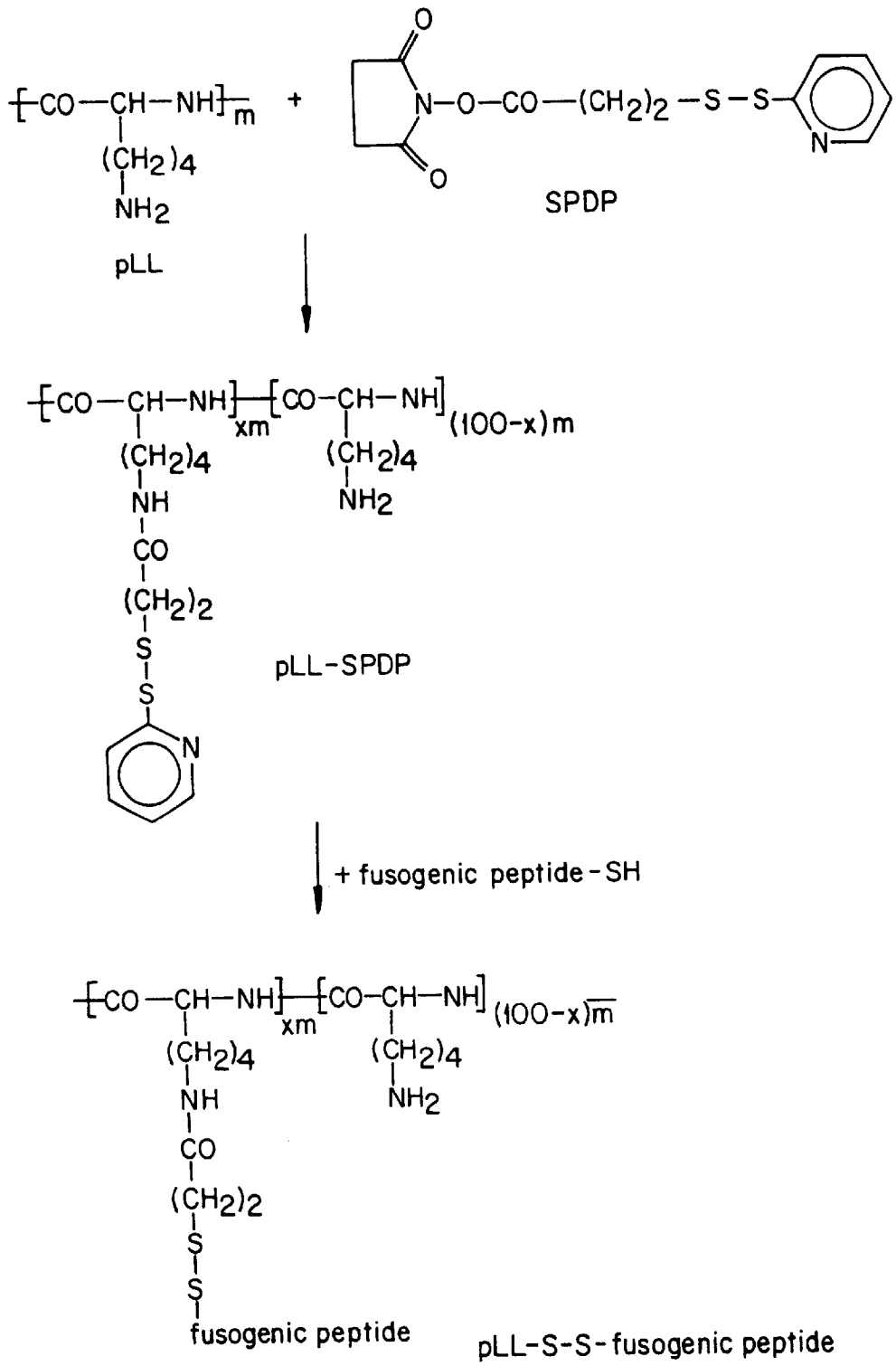
FIG. 11 a diagram of the synthesis of pLL-g-pEG via labile —S—S— bond.

This reaction scheme is illustrated in FIG. 11 of the drawings.

In the various examples herein presented, in general the cationic polymer and/or the hydrophilic coating polymer has been described as having only one kind of reactive group for bonding the hydrophilic polymer to the cationic core and for coupling other molecular entities such as targeting moieties, membrane disrupting or fuisogenic agents, nuclear homing groups etc. It is also possible, however, to form the cationic polymer and/or the hydrophilic coating polymer with two or more kinds of reactive groups having different chemical reactivities, e.g. ONp and SH or ONp and biotin. This may sometimes be advantageous for enabling a better degree of control to be achieved in respect of the different coupling reactions and rendering the extent of reactions in the initial coupling reactions to be less critical than otherwise may be the case.

In some cases it may be useful to carry out the preparation of the nucleic acid delivery vehicles in organic solvents whereby any hydrolytic action during the stage of coating the complexes with the hydrophilic material can be limited, thus improving definition of the products. Such solvents could be selected from chloroform, methylene chloride and dimethyl sulfoxide.

This is illustrated in the example given below of the synthesis of a polymer such as DEXTRAN or pHEG provided with both reactive p-nitrophenyl ester and 2-pyridyidithio reactive groups.

Example 17

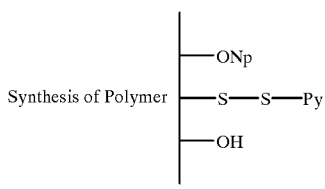

Stage 1—Synthesis of Polymer—NH$_2$

The polymer (dextran, PHEG, etc.) is modified via chloroformate activation and subsequent coupling with triethyleneglycoldiamine:

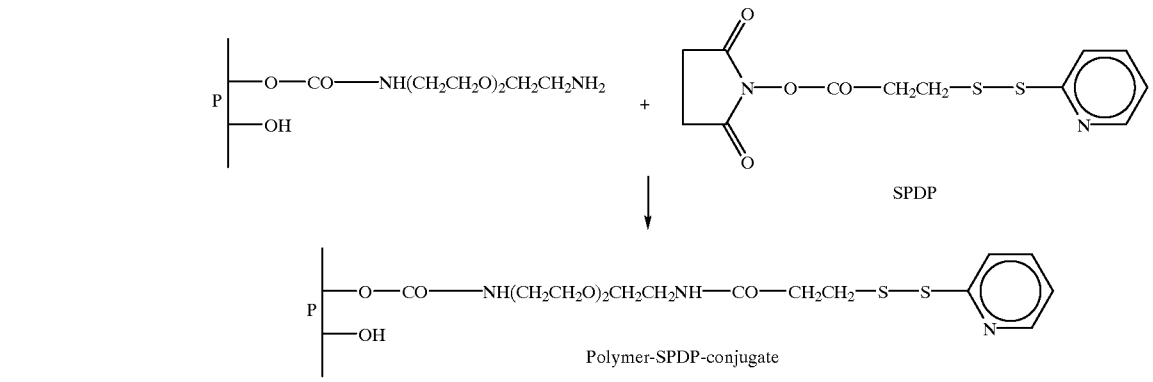

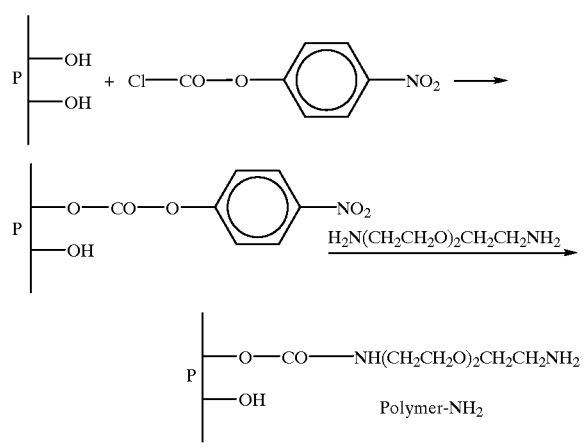

The experimental procedure is given for the modification of dextran. It could be applied for other polymers as PHEG, other polysaccharides, etc.

DEXTRAN (1 gram) is dissolved in mixture of 30 ml dimethylsulfoxide and 30 ml pyridine. 4-Nitrophenylchloroformate (0,125 g) is added under stirring. 4-Dimethylaminopyridine is used as a catalyst. After 4 hrs reaction at 0° C. the product is isolated by precipitation into methanol/ether, filtration and drying under vacuum.

The degree of substitution, determined by $^1$H NMR, is 5%.

In the next step the activated DEXTRAN (1 gram) is dissolved in a mixture of 30 ml dimethylsulfoxide and 30 ml pyridine. Triethyleneglycoldiamine (2 ml) is added dropwise. The solution is stirred during 48 hrs at room temperature. The polymer is precipitated into hexane/ethylacetate, filtered and dried under vacuum.

The polymer is characterised by $^1$H NMR and by UV-spectroscopy using ortho-phtalic dicarboxaldehyde (OPA)-method for determination of the degree of substitution (amount of NH$_2$-groups). The degree of substitution corresponds to the % of ONp-groups in activated dextran (5%).

Stage 2—Synthesis of Polymer—SPDP—Conjugate

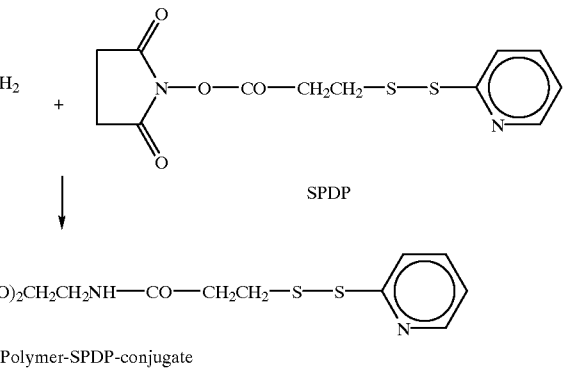

Dextran-NH$_2$ (1 gram) is dissolved in 20 ml dimethylsulfoxide. The solution of SPDP (0.48 g) in 32 ml dimethylsulfoxide is added dropwise to the solution of DEXTRAN-NH$_2$ under stirring. 4-Dimethylaminopyridine is used as a catalyst. The reaction mixture is stirred for 24 hrs at room temperature. The conjugate is isolated by precipitation in cold ethanol/ether. The product is further purified by preparative size exclusion chromatography on a SEPHADEX G-25 column followed by lyophilization.

The degree of substitution (5 mol %) is determined by UV-spectroscopy after the reaction of the polymer with dithiotreitol (DTT). The concentration of the released pyridine-2-thione, determined by its absorption at 343 nm, is equivalent to the concentration of the pyridyldithi6-end groups.

The degree of substitution corresponds to the % of the amino groups in Polymer—NH$_2$ conjugate.

The same procedure could be applied for coupling of N-hydroxysuccinimine ester of Biotin etc.

Stage 3—Activation of Polymer-SPDP-Conjugate

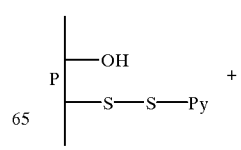

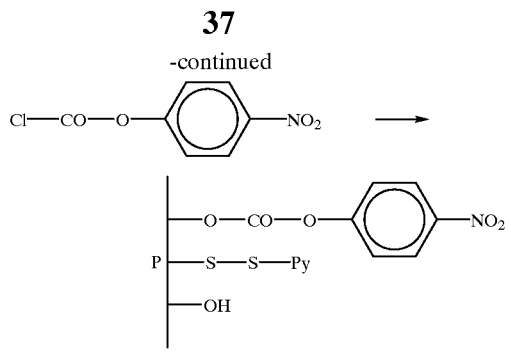

DEXTRAN-SPDP-conjugate (1 gram) is dissolved in mixture of 30 ml DMSO and 30 ml pyridine. 4-Nitrophenylchloroformate (0,375 g) is added under stirring. Dimethylaminopyridine is used as a catalyst. After 4 hrs reaction at 0° C. the product is isolated by precipitation into methanol/ether, filtration and drying under vacuum. The polymer is fuirther purified by dialysis against water and isolated by lyophilization.

The degree of substitution with QNp-groups, determined by $^1$H NR is 15%.

Some physicochemical properties of complexes formed in accordance with the invention have been evaluated using agarose gel electrophoresis, atomic force microscopy and zeta potential measurement. Compared with corresponding complexes formed using just the appropriate polycationic polymer to condense the DNA without a hydrophilic polymer coating, it has been found that surface charge as measured by zeta potential is significantly decreased compared with equivalent polycation/DNA complexes in each. case. Also, atomic force microscopy showed that the complexes are generally discrete spheres similar to those formed between DNA and simple polycations. Overall, however, it is clear that the stepwise efficient self-assembly of cationic polymers with nucleic acid material followed by coating with hydrophilic polymer material can yield complexes with properties quite different from those of complexes formed between DNA and simple polycations alone, and manipulation of the chemical structure of the polymers and the charge ratio of formation can significantly influence the physicochemical and other characteristics of the complexes produced.

As will be seen, the invention presents a number of different aspects and it embraces within its scope all novel and inventive features and aspects herein disclosed, either explicitly or implicitly and either singly or in combination with one another. Also, many modifications are possible and, in particular, the scope of the invention is not to be construed as being limited by the illustrative examples or by the terms and expressions used herein merely in a descriptive or explanatory sense.

What is claimed is:

1. A method of constructing a synthetic polymer-based carrier vehicle for delivery of nucleic acid material to target cells in biological systems, wherein said method comprises carrying out separately but sequentially the steps of:
   (a) bringing the nucleic acid material into association with cationic polyelectrolyte polymer material to form by self-assembly therebetween a polyelectrolyte complex which provides a nucleic acid containing cationic polymer core for said carrier vehicle, and
   (b) reacting said polyelectrolyte complex with reactive hydrophilic polymer material whereby the latter bonds to said complex and forms a hydrophilic coating that provides an outer protective steric shield and assists in stabilising the complex, so that a synthetic polymer-based carrier vehicle for delivery of nucleic acid material is formed,
   said hydrophilic polymer material being composed of a synthetic polymer backbone having side chains which terminate in reactive groups and which contain an oligopeptide spacer, said hydrophilic polymer material including between 4% and 10% of said oligopeptide spacer containing side chains, so that the synthetic polymer-based vehicle is constructed.

2. A method as claimed in claim 1 wherein the molecules of both the hydrophilic polymer material and the cationic polyelectrolyte polymer material have reactive groups that react to attach or link the hydrophilic polymer material to said cationic polyelectrolyte polymer material by way of covalent bonds.

3. A method as claimed in claim 1 or 2 wherein the hydrophilic coating polymer is a copolymer based on N-2 hydroxypropylmethacrylamide (HPMA).

4. A method as claimed in claim 1 or 2 wherein specific cell targeting groups are attached to the cationic polymer core or to the hydrophilic coating polymer material.

5. A method as claimed in claim 1 or 2 wherein the cationic polyelectrolyte polymer material is composed of polyamine molecules.

6. A method as claimed in claim 1 or 2 wherein the cationic polyelectrolyte polymer material is a polymer of acrylic or methacrylic monomers.

7. A method as claimed in claim 1 or 2 in which the cationic polyelectrolyte polymer material incorporates reactive binding groups selected from the group consisting of biotin, avidin and streptavidin.

8. A method as claimed in claim 1 or 2 wherein the molecules of the hydrophilic polymer material are multivalent with a plurality of reactive groups that form a plurality of cross-linkages with the nucleic acid containing cationic polymer core of the polyelectrolyte complex.

9. A method as claimed in claim 1 or 2 in which the oligopeptide spacer forms a linkage that is acid labile, hydrolytically unstable or enzymatically biodegradable.

10. A method as claimed in claim 1 or 2 in which said oligopeptide spacer forms a linkage that is acid labile, whereby the hydrophilic polymer coat is released when introduced into an intracellular acidic environment.

11. A method as claimed in claim 1 or 2 wherein the oligopeptide spacer containing side chains terminate in reactive esters.

12. A method as claimed in claim 1 or 2 wherein the oligopeptide spacer containing side chains terminate in carboxylic acid groups.

13. A method as claimed in claim 1 or 2 in which the oligopeptide spacer in the side chains is a tetrapeptide.

14. A method as claimed in claim 1 or 2 in which the molecules of the hydrophilic polymer material contain backbones comprised of blocks of poly(ethyleneglycol) (pEG) joined end to end by biodegradable sequences bearing pendant reactive groups.

15. A method as claimed in claim 1 or 2 wherein the nucleic acid material is DNA.

16. A method as claimed in claim 1 or 2 in which a fusogenic peptide or lipid based membrane disrupting agent which enables entry into cells is incorporated in the polyelectrolyte complex which is reacted with the hydrophilic polymer material.

17. A method as claimed in claim 1 or 2 wherein the molecules of the hydrophilic polymer material include biodegradable components or linkages in the main chain backbone thereof.

18. A method as claimed in claim 1 or 2 wherein the nucleic acid material is contained in a DNA expression vector.

19. A method as claimed in claim 1 or 2 wherein the nucleic acid material is selected from the group consisting of exogeneous gene containing plasmid DNA, RNA, antisense nucleic acid and oligonucleotides.

20. A method as claimed in claim 1 or 2 wherein fusogenic molecules are incorporated into the polyelectrolyte complex, which fusogenic molecules are adapted to be released after removal or degradation of the hydrophilic polymer coating upon uptake by target cells.

21. A method as claimed in claim 1 or 2 wherein the cationic polyelectrolyte polymer material is pH responsive such that its degree of protonation changes in an acidic environment as occurs in the endosomal compartment of mammalian cells.

22. A method as claimed in claim 1 or 2 wherein the cationic polymer material contains a mixture of different types of amino groups of which some are predominantly charged at neutral pH while others become protonated and charged at lower pH as occurs in the endosomal compartment of mammalian cells.

23. A synthetic polymer-based carrier vehicle for delivery of nucleic acid material to target cells in biological systems made by the method as claimed in claim 1 or 2.

24. A method as claimed in claim 4 wherein the targeting groups are selected from the group consisting of growth factors and antibodies.

25. A method as claimed in claim 5 wherein the polyamine molecules have a molecular weight in the range of 3 to 25 kD.

26. A method as claimed in claim 5 wherein the cationic polyelectrolyte polymer material is composed of a polyamine selected from the group consisting of poly(L)lysine and poly(L)ornithine.

27. A method as claimed in claim 8 wherein the hydrophilic polymer material contains reactive aldehyde groups adapted to react with amino group-bearing or hydrazide-bearing cationic polyelectrolyte polymer material in said cationic polymer core.

28. A method as claimed in claim 8 wherein the hydrophilic polymer material forming the coating comprises more than one kind of hydrophilic polymer.

29. A method as claimed in claim 8 in which the molecules of the hydrophilic polymer material contain backbones comprised of poly[N-(2-hydroxyethyl)-L-glutamine] (pHEG) bearing pendant reactive groups and side chains incorporating poly(etliyleneglycol) (pEG).

30. A method as claimed in claim 11 in which the reactive esters are selected from the group consisting of p-nitrophenyl esters, reactive nitrophenoxy esters, and succinimidyl esters.

31. A method as claimed in claim 13 in which said tetrapeptide is selected from the group consisting of glycine-phenylalanine-leucine-glycine (SEQ ID NO:1), glycine-phenylalaninc-alanine-leucine (SEQ ID NO:2) and glycine-leucine phenylalanine-glycine (SEQ ID NO:3).

32. A method as claimed in claim 14 in which said pendant reactive groups are reactive esters.

33. A method as claimed in claim 15 in which the charge ratio of the cationic polyelectrolyte polymer material to DNA is within the range 0.7 to 4.2.

34. A method as claimed in claim 15 in which the hydrophilic polymer material is added to the DNA containing polyelectrolyte complex under reaction conditions which include a temperature within the range of 15 to 37° C. and a pH of 7 to 7.6.

35. A method as claimed in claim 5 in which the polyamine molecules are partially modified by reacting with N-succinimidyl 3-(2-pyridyldithio)propionate (SPDP) before self assembly with the nucleic acid material.

36. A method as claimed in claim 35 wherein the reactive hydrophilic polymer material which is reacted with the polyelectrolyte complex comprises molecules composed of a hydrophilic polymeric block having at least one reactive thiol group whereby the molecules of the hydrophilic polymer material are grafted onto the backbone of the polyamine polymer molecules via labile disulfide (S—S) bonds.

37. A method as claimed in claim 36 wherein the hydrophilic polymer material is a polyethylene glycol having a reactive thiol group.

38. A method as claimed in claim 6 in which the cationic polyelectrolyte polymer material is a polymer or copolymer composed of monomers selected from the group consisting of methacryloyl-2-amidoethylene diamine, methacryloyl glycyl-2-amidoethylene diamine, methacryloyl diglycyl-2-amidoethylene diamine, methacryloyl-6-hexamethylene diamine, methacryloyl glycyl-6-hexamethylene diamine, and methacryloyl diglycyl-6-hexamethylene diamine, and has at least one reactive amino or alkyl amino functional group.

39. A method as claimed in claim 38 wherein the polymer or copolymer of said cationic polyelectrolyte polymer material terminates in a carboxylic end group.

40. A method as claimed in claim 38 wherein the polymer or copolymer of said cationic polyelectrolyte polymer material has a main chain and side chains. which side chains terminate in primary amino groups.

41. A method as claimed in claim 15 wherein the cationic polyelectrolyte polymer material is added to the DNA in aqueous solution at a pH of less than 8.0.

42. A method as claimed in claim 41 in which the DNA concentration is less than 80 μg per ml.

43. A method as claimed in claim 42 in which the DNA entration is within the range of 20 to 50 μg per ml.

44. A carrier vehicle as claimed in claim 23 wherein said carrier vehicle is in the form of particles having a maximum diameter <70 nm.

45. A carrier vehicle as claimed in claim 44 wherein the maximum diameter of said particles, as determined by atomic force microscopy, is in the range of 30–50 nm.

46. A method of constructing a synthetic polymer-based carrier vehicle for delivery of nucleic acid material to target cells in biological systems, wherein said method comprises carrying out separately but sequentially the steps of:

(a) bringing the nucleic acid material into association with cationic polyelectrolyte polymer material to form by self-assembly therebetween a polyelectrolyte complex which provides a nucleic acid containing cationic polymer core for said carrier vehicle, and (b) reacting said polyelectrolyte complex with reactive hydrophilic polymer material whereby the latter bonds to said complex and forms a hydrophilic coating that provides an outer protective steric shield and assists in stabilising the complex, so that a synthetic polymer-based carrier vehicle for delivery of nucleic acid material is formed, said carrier vehicle being in the form of a particle having a maximum diameter, as determined by atomic force microscopy, in the range of 30 to 50 nm.

47. A synthetic polymer based carrier vehicle for delivery of nucleic acid material to target cells in biological systems made by a method which comprises carrying out separately but sequentially the steps of:

(a) bringing the nucleic acid material into association with cationic polyelectrolyte polymer material to form by self-assembly therebetween a polyelectrolyte complex which provides a nucleic acid containing cationic polymer core for said carrier vehicle, and (b) reacting said polyelectrolyte complex with reactive hydrophilic polymer material whereby the latter bonds to said complex and forms a hydrophilic coating that provides an outer protective steric shield and assists in stabilising the complex, so that a synthetic polymer-based carrier vehicle for delivery of nucleic acid material is formed, said carrier vehicle being in the form of particles having a diameter between 30 and 50 nm, as determined by atomic force microscopy.

48. A method of constructing a synthetic polymer-based carrier vehicle for delivery of nucleic acid material to target cells in biological systems, wherein said method comprises carrying out separately but sequentially the steps of:

(a) bringing the nucleic acid material into association with cationic polyelectrolyte polymer material to form by self-assembly therebetween a polyelectrolyte complex which provides a nucleic acid containing cationic polymer core for said carrier vehicle, and (b) reacting said polyelectrolyte complex with reactive hydrophilic polymer material whereby the latter bonds to said complex and forms a hydrophilic coating that provides an outer protective steric shield and assists in stabilising the complex, so that a synthetic polymer-based carrier vehicle for delivery of nucleic acid material is formed, said reactive hydrophilic polymer material being composed of multivalent molecules of poly-N-(2-hydroxyethyl)-L-glutamine (pHEG) having side chains terminating in reactive groups that form a plurality of cross-linkages with the nucleic acid containing cationic polymer core of the polyelectrolyte complex.

49. A method as claimed in claim 48 wherein the molecules of the reactive hydrophilic polymer material and of the cationic polyelectrolyte polymer material react to attach or link said hydrophilic polymer material to the cationic polymer material by way of covalent bonds.

50. A method as claimed in claim 48 or 49 in which the reactive groups are reactive esters.

51. A method as claimed in claim 48 or 49 in which the nucleic acid material is DNA.

52. A synthetic polymer-based carrier vehicle for delivery of nucleic acid material to target cells in biological systems made by the method claimed in claim 48 or 49.

* * * * *

SEQUENCE LISTING

```
<160> NUMBER OF SEQ ID NOS:  3

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Leu Gly
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Ala Leu
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 3

Gly Leu Phe Gly
```